US009139592B2

(12) United States Patent
Batist et al.

(10) Patent No.: US 9,139,592 B2
(45) Date of Patent: Sep. 22, 2015

(54) MODULATORS OF NRF2 AND USES THEREOF

(75) Inventors: Gerald Batist, Montreal (CA); Jian Hui Wu, Montreal (CA)

(73) Assignee: TRT PHARMA INC., Montreal (CA)

(*) Notice: Subject to any disclaimer, the term of this patent is extended or adjusted under 35 U.S.C. 154(b) by 155 days.

(21) Appl. No.: 13/704,449

(22) PCT Filed: May 31, 2011

(86) PCT No.: PCT/CA2011/000649
§ 371 (c)(1),
(2), (4) Date: Dec. 14, 2012

(87) PCT Pub. No.: WO2011/156889
PCT Pub. Date: Dec. 22, 2011

(65) Prior Publication Data
US 2013/0137694 A1 May 30, 2013

Related U.S. Application Data

(60) Provisional application No. 61/354,332, filed on Jun. 14, 2010.

(51) Int. Cl.
*C07D 487/04* (2006.01)
*A61K 31/00* (2006.01)
(Continued)

(52) U.S. Cl.
CPC .............. *C07D 487/04* (2013.01); *A61K 31/00* (2013.01); *A61K 31/353* (2013.01); *A61K 31/4433* (2013.01); *A61K 31/473* (2013.01); *A61K 31/5025* (2013.01); *A61K 31/519* (2013.01); *A61K 31/52* (2013.01); *C07D 219/06* (2013.01); *C07D 311/22* (2013.01);
(Continued)

(58) Field of Classification Search
CPC . A61K 31/4433; C07D 311/32; C07D 311/22
See application file for complete search history.

(56) References Cited

U.S. PATENT DOCUMENTS

2009/0069301 A1    3/2009   Milburn et al.

FOREIGN PATENT DOCUMENTS

CA        1167844-X        5/1984
CA        1170260-X        7/1984
(Continued)

OTHER PUBLICATIONS

Shih-Ching Lo et al., The EMBO Journal (2006) 25, 3605-3617.*
(Continued)

*Primary Examiner* — Savitha Rao
*Assistant Examiner* — Angela Brown-Pettigrew
(74) *Attorney, Agent, or Firm* — Benoit & Cote Inc.

(57) ABSTRACT

The present invention is directed to a pharmaceutical composition comprising the following compound

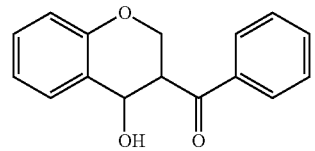

or a pharmaceutically acceptable salt thereof. The compound is a modulator of Nrf2 protein and binds at least one of the BTB domain, IVR domain and Kelch domain of Keap1 protein, activating or inhibiting Nrf2.

1 Claim, 10 Drawing Sheets

(51) Int. Cl.

| | |
|---|---|
| *A61K 31/353* | (2006.01) |
| *A61K 31/4433* | (2006.01) |
| *A61K 31/473* | (2006.01) |
| *A61K 31/5025* | (2006.01) |
| *A61K 31/519* | (2006.01) |
| *A61K 31/52* | (2006.01) |
| *C07D 219/06* | (2006.01) |
| *C07D 311/22* | (2006.01) |
| *C07D 311/32* | (2006.01) |
| *C07D 473/16* | (2006.01) |
| *C07D 473/24* | (2006.01) |
| *C07D 473/40* | (2006.01) |

(52) U.S. Cl.
CPC ........... *C07D 311/32* (2013.01); *C07D 473/16* (2013.01); *C07D 473/24* (2013.01); *C07D 473/40* (2013.01)

(56) References Cited

FOREIGN PATENT DOCUMENTS

| CA | 1242440-X | 9/1988 |
|---|---|---|
| CA | 2240439-X | 7/1997 |
| CA | 2263913-X | 3/1998 |
| CA | 2250258-X | 7/1998 |
| CA | 2348391-X | 5/2000 |
| CA | 2400394-X | 8/2001 |
| CA | 2464593-X | 5/2003 |
| CA | 2522338-X | 2/2005 |
| CA | 2541590-X | 4/2005 |
| CA | 2584209-X | 4/2006 |
| CA | 2653941-X | 12/2007 |
| CA | 2684638-X | 10/2008 |
| WO | WO 2005032559-X | 4/2005 |

OTHER PUBLICATIONS

Bellassoued-Fargeau et al (J. Heterocyclic Chem., 22, 45 (1985) pp. 45-46).*
Bellassoued-Fargeau et al, translation.*
Patani et al. (Chem. Rev. 1996, vol. 96, pp. 3147-3176).*
Bellassoued-Fargeau et al, translation (1985).*
International Searching Authority, International Search Report, (Aug. 12, 2011) 5 pages.
Wang. W, Ho W.C,Dicker.D.T, Winkler.J.D, Marmostein R and El-Deiry W. Acridine Derivatives Activate p53 and induce Tumor Cell Death through Bax. Cancer Biology and therapy, vol. 4, Issue No. 8, pp. 893-898 (2005).
Wu, J. H: Miao; W,Hu.L.G and Batist.G. Identification and characterization of novel Nrf2 Inducers Designed to Target the Intervening Region of Keap1. Chemical Biology and drug Design; vol. 75: pp. 475-480. May 2010 ISSN 1747-02777.

\* cited by examiner

1) Full length sequence of human Keap1 (1-624) (SEQ ID NO:1)

MQPDPRPSGAGACCRFLPLQSQCPEGAGDAVMYASTECKAEVTPSQHGNRTFSYTLEDH
TKQAFGIMNELRLSQQLCDVTLQVKYQDAPAAQFMAHKVVLASSSPVFKAMFTNGLREQ
GMEVVSIEGIHPKVMERLIEFAYTASISMGEKCVLHVMNGAVMYQIDSVVRACSDFLVQ
QLDPSNAIGIANFAEQIGCVELHQRAREYIYMHFGEVAKQEEFFNLSHCQLVTLISRDD
LNVRCESEVFHACINWVKYDCEQRRFYVQALLRAVRCHSLTPNFLQMQLQKCEILQSDS
RCKDYLVKIFEELTLHKPTQVMPCRAPKVGRLIYTAGGYFRQSLSYLEAYNPSDGTWLR
LADLQVPRSGLAGCVVGGLLYAVGGRNNSPDGNTDSSALDCYNPMTNQWSPCAPMSVPR
NRIGVGVIDGHIYAVGGSHGCIHHNSVERYEPERDEWHLVAPMLTRRIGVGVAVLNRLL
YAVGGFDGTNRLNSAECYYPERNEWRMITAMNTIRSGAGVCVLHNCIYAAGGYDGQDQL
NSVERYDVETETWTFVAPMKHRRSALGITVHQGRIYVLGGYDGHTFLDSVECYDPDTDT
WSEVTRMTSGRSGVGVAVTMEPCRKQIDQQNCTC

2) BTB domain (amino acids 67 - 170) of human Keap1 (SEQ ID NO:2)

MNELRLSQQLCDVTLQVKYQDAPAAQFMAHKVVLASSSPVFKAMFTNGLREQGMEVVSI
EGIHP KVMERLIEFAYTASISMGEKCVLHVMNGAVMYQIDSVVRA

3) IVR domain (amino acids 180 - 314) of human Keap1 (SEQ ID NO:3)

DPSNAIGIANFAEQIGCVELHQRAREYIYMHFGEVAKQEEFFNLSHCQLVTLISRDDLN
VRCESEVFHACINWVKYDCEQRRFYVQALLRAVRCHSLTPNFLQMQLQKCEILQSDSRC
KDYLVKIFEELTLHKPT

4) Kelch domain (amino acids 315 - 598) of human Keap1 (SEQ ID NO:4)

QVMPCRAPKVGRLIYTAGGYFRQSLSYLEAYNPSDGTWLRLADLQVPRSGLAGCVVGGL
LYAVGGRNNSPDGNTDSSALDCYNPMTNQWSPCAPMSVPRNRIGVGVIDGHIYAVGGSH
GCIHHNSVERYEPERDEWHLVAPMLTRRIGVGVAVLNRLLYAVGGFDGTNRLNSAECYY
PERNEWRMITAMNTIRSGAGVCVLHNCIYAAGGYDGQDQLNSVERYDVETETWTFVAPM
KHRRSALGITVHQGRIYVLGGYDGHTFLDSVECYDPDTDTWSEVTRMT

Fig. 10

SEQUENCE LISTING

<160> NUMBER OF SEQ ID NOS: 4

<210> SEQ ID NO 1
<211> LENGTH: 624
<212> TYPE: PRT
<213> ORGANISM: Homo sapiens

<400> SEQUENCE: 1

Met Gln Pro Asp Pro Arg Pro Ser Gly Ala Gly Ala Cys Cys Arg Phe
1               5                   10                  15

Leu Pro Leu Gln Ser Gln Cys Pro Glu Gly Ala Gly Asp Ala Val Met
            20                  25                  30

Tyr Ala Ser Thr Glu Cys Lys Ala Glu Val Thr Pro Ser Gln His Gly
        35                  40                  45

Asn Arg Thr Phe Ser Tyr Thr Leu Glu Asp His Thr Lys Gln Ala Phe
    50                  55                  60

Gly Ile Met Asn Glu Leu Arg Leu Ser Gln Gln Leu Cys Asp Val Thr
65                  70                  75                  80

Leu Gln Val Lys Tyr Gln Asp Ala Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
            115                 120                 125

His Pro Lys Val Met Glu Arg Leu Ile Glu Phe Ala Tyr Thr Ala Ser
    130                 135                 140

Ile Ser Met Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190

Gln Ile Gly Cys Val Glu Leu His Gln Arg Ala Arg Glu Tyr Ile Tyr
        195                 200                 205

Met His Phe Gly Glu Val Ala Lys Gln Glu Glu Phe Phe Asn Leu Ser
    210                 215                 220

His Cys Gln Leu Val Thr Leu Ile Ser Arg Asp Asp Leu Asn Val Arg
225                 230                 235                 240

Cys Glu Ser Glu Val Phe His Ala Cys Ile Asn Trp Val Lys Tyr Asp
                245                 250                 255

Cys Glu Gln Arg Arg Phe Tyr Val Gln Ala Leu Leu Arg Ala Val Arg
            260                 265                 270

Cys His Ser Leu Thr Pro Asn Phe Leu Gln Met Gln Leu Gln Lys Cys
        275                 280                 285

Glu Ile Leu Gln Ser Asp Ser Arg Cys Lys Asp Tyr Leu Val Lys Ile
    290                 295                 300

Phe Glu Glu Leu Thr Leu His Lys Pro Thr Gln Val Met Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asp Gly Thr Trp
            340                 345                 350

Leu Arg Leu Ala Asp Leu Gln Val Pro Arg Ser Gly Leu Ala Gly Cys
        355                 360                 365

```
Val Val Gly Gly Leu Leu Tyr Ala Val Gly Arg Asn Asn Ser Pro
    370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Pro Met Ser Val Pro Arg Asn Arg Ile
                405                 410                 415

Gly Val Gly Val Ile Asp Gly His Ile Tyr Ala Val Gly Gly Ser His
            420                 425                 430

Gly Cys Ile His His Asn Ser Val Glu Arg Tyr Glu Pro Glu Arg Asp
                435                 440                 445

Glu Trp His Leu Val Ala Pro Met Leu Thr Arg Arg Ile Gly Val Gly
    450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
                485                 490                 495

Trp Arg Met Ile Thr Ala Met Asn Thr Ile Arg Ser Gly Ala Gly Val
            500                 505                 510

Cys Val Leu His Asn Cys Ile Tyr Ala Ala Gly Gly Tyr Asp Gly Gln
    515                 520                 525

Asp Gln Leu Asn Ser Val Glu Arg Tyr Asp Val Glu Thr Glu Thr Trp
    530                 535                 540

Thr Phe Val Ala Pro Met Lys His Arg Arg Ser Ala Leu Gly Ile Thr
545                 550                 555                 560

Val His Gln Gly Arg Ile Tyr Val Leu Gly Gly Tyr Asp Gly His Thr
                565                 570                 575

Phe Leu Asp Ser Val Glu Cys Tyr Asp Pro Asp Thr Asp Thr Trp Ser
            580                 585                 590

Glu Val Thr Arg Met Thr Ser Gly Arg Ser Gly Val Gly Val Ala Val
    595                 600                 605

Thr Met Glu Pro Cys Arg Lys Gln Ile Asp Gln Gln Asn Cys Thr Cys
610                 615                 620

<210> SEQ ID NO 2
<211> LENGTH: 104
<212> TYPE: PRT
<213> ORGANISM: Homo sapiens

<400> SEQUENCE: 2

Met Asn Glu Leu Arg Leu Ser Gln Gln Leu Cys Asp Val Thr Leu Gln
1               5                   10                  15

Val Lys Tyr Gln Asp Ala Pro Ala Ala Gln Phe Met Ala His Lys Val
                20                  25                  30

Val Leu Ala Ser Ser Ser Pro Val Phe Lys Ala Met Phe Thr Asn Gly
            35                  40                  45

Leu Arg Glu Gln Gly Met Glu Val Val Ser Ile Glu Gly Ile His Pro
    50                  55                  60

Lys Val Met Glu Arg Leu Ile Glu Phe Ala Tyr Thr Ala Ser Ile Ser
65                  70                  75                  80

Met Gly Glu Lys Cys Val Leu His Val Met Asn Gly Ala Val Met Tyr
                85                  90                  95

Gln Ile Asp Ser Val Val Arg Ala
            100
```

```
<210> SEQ ID NO 3
<211> LENGTH: 135
<212> TYPE: PRT
<213> ORGANISM: Homo sapiens

<400> SEQUENCE: 3
```

| | | | | | | | | | | | | | | |
|---|---|---|---|---|---|---|---|---|---|---|---|---|---|---|
| Asp | Pro | Ser | Asn | Ala | Ile | Gly | Ile | Ala | Asn | Phe | Ala | Glu | Gln | Ile | Gly |
| 1 | | | | 5 | | | | | 10 | | | | | 15 | |
| Cys | Val | Glu | Leu | His | Gln | Arg | Ala | Arg | Glu | Tyr | Ile | Tyr | Met | His | Phe |
| | | | 20 | | | | | 25 | | | | | 30 | | |
| Gly | Glu | Val | Ala | Lys | Gln | Glu | Glu | Phe | Phe | Asn | Leu | Ser | His | Cys | Gln |
| | | | | 35 | | | | | 40 | | | | | 45 | |
| Leu | Val | Thr | Leu | Ile | Ser | Arg | Asp | Asp | Leu | Asn | Val | Arg | Cys | Glu | Ser |
| | 50 | | | | | 55 | | | | | 60 | | | | |
| Glu | Val | Phe | His | Ala | Cys | Ile | Asn | Trp | Val | Lys | Tyr | Asp | Cys | Glu | Gln |
| 65 | | | | | 70 | | | | | 75 | | | | | 80 |
| Arg | Arg | Phe | Tyr | Val | Gln | Ala | Leu | Leu | Arg | Ala | Val | Arg | Cys | His | Ser |
| | | | | 85 | | | | | 90 | | | | | 95 | |
| Leu | Thr | Pro | Asn | Phe | Leu | Gln | Met | Gln | Leu | Gln | Lys | Cys | Glu | Ile | Leu |
| | | | 100 | | | | | 105 | | | | | 110 | | |
| Gln | Ser | Asp | Ser | Arg | Cys | Lys | Asp | Tyr | Leu | Val | Lys | Ile | Phe | Glu | Glu |
| | | | | 115 | | | | | 120 | | | | | 125 | |
| Leu | Thr | Leu | His | Lys | Pro | Thr | | | | | | | | | |
| | 130 | | | | | 135 | | | | | | | | | |

```
<210> SEQ ID NO 4
<211> LENGTH: 284
<212> TYPE: PRT
<213> ORGANISM: Homo sapiens

<400> SEQUENCE: 4
```

| | | | | | | | | | | | | | | |
|---|---|---|---|---|---|---|---|---|---|---|---|---|---|---|---|
| Gln | Val | Met | Pro | Cys | Arg | Ala | Pro | Lys | Val | Gly | Arg | Leu | Ile | Tyr | Thr |
| 1 | | | | 5 | | | | | 10 | | | | | 15 | |
| Ala | Gly | Gly | Tyr | Phe | Arg | Gln | Ser | Leu | Ser | Tyr | Leu | Glu | Ala | Tyr | Asn |
| | | | 20 | | | | | 25 | | | | | 30 | | |
| Pro | Ser | Asp | Gly | Thr | Trp | Leu | Arg | Leu | Ala | Asp | Leu | Gln | Val | Pro | Arg |
| | | | | 35 | | | | | 40 | | | | | 45 | |
| Ser | Gly | Leu | Ala | Gly | Cys | Val | Val | Gly | Gly | Leu | Leu | Tyr | Ala | Val | Gly |
| | 50 | | | | | 55 | | | | | 60 | | | | |
| Gly | Arg | Asn | Asn | Ser | Pro | Asp | Gly | Asn | Thr | Asp | Ser | Ser | Ala | Leu | Asp |
| 65 | | | | | 70 | | | | | 75 | | | | | 80 |
| Cys | Tyr | Asn | Pro | Met | Thr | Asn | Gln | Trp | Ser | Pro | Cys | Ala | Pro | Met | Ser |
| | | | | 85 | | | | | 90 | | | | | 95 | |
| Val | Pro | Arg | Asn | Arg | Ile | Gly | Val | Gly | Val | Ile | Asp | Gly | His | Ile | Tyr |
| | | | 100 | | | | | 105 | | | | | 110 | | |
| Ala | Val | Gly | Gly | Ser | His | Gly | Cys | Ile | His | His | Asn | Ser | Val | Glu | Arg |
| | | | | 115 | | | | | 120 | | | | | 125 | |
| Tyr | Glu | Pro | Glu | Arg | Asp | Glu | Trp | His | Leu | Val | Ala | Pro | Met | Leu | Thr |
| | 130 | | | | | 135 | | | | | 140 | | | | |
| Arg | Arg | Ile | Gly | Val | Gly | Val | Ala | Val | Leu | Asn | Arg | Leu | Leu | Tyr | Ala |
| 145 | | | | | 150 | | | | | 155 | | | | | 160 |
| Val | Gly | Gly | Phe | Asp | Gly | Thr | Asn | Arg | Leu | Asn | Ser | Ala | Glu | Cys | Tyr |
| | | | | 165 | | | | | 170 | | | | | 175 | |
| Tyr | Pro | Glu | Arg | Asn | Glu | Trp | Arg | Met | Ile | Thr | Ala | Met | Asn | Thr | Ile |
| | | | 180 | | | | | 185 | | | | | 190 | | |

```
Arg Ser Gly Ala Gly Val Cys Val Leu His Asn Cys Ile Tyr Ala Ala
        195                 200                 205

Gly Gly Tyr Asp Gly Gln Asp Gln Leu Asn Ser Val Glu Arg Tyr Asp
        210                 215                 220

Val Glu Thr Glu Thr Trp Thr Phe Val Ala Pro Met Lys His Arg Arg
225                 230                 235                 240

Ser Ala Leu Gly Ile Thr Val His Gln Gly Arg Ile Tyr Val Leu Gly
                245                 250                 255

Gly Tyr Asp Gly His Thr Phe Leu Asp Ser Val Glu Cys Tyr Asp Pro
                260                 265                 270

Asp Thr Asp Thr Trp Ser Glu Val Thr Arg Met Thr
        275                 280
```

MODULATORS OF NRF2 AND USES THEREOF

CROSS-REFERENCE TO RELATED APPLICATIONS

This application is the U.S. National Stage of International Application No. PCT/CA62011/000649, filed May 31, 2011, which designates the U.S., published in English, and which claims the benefit of U.S. Provisional Application No. 61/354,332, filed Jun.14, 2010, the specification of which is hereby incorporated by reference.

BACKGROUND (a) Field

The subject matter disclosed generally relates to modulators of Nrf2, and more specifically to compounds which binds at least one of the BTB domain, IVR domain and Kelch domain of Keap1 protein, activating or inhibiting Nrf2.

(b) Related Prior Art

As chemical carcinogenesis likely plays a role in cancer development, cytoprotective enzyme induction is believed to be an important means of cancer chemoprevention. Transcription factor nuclear factor-erythroid 2-related factor 2 (Nrf2) regulates a battery of genes encoding carcinogen-detoxifying enzymes and antioxidant proteins by binding to the antioxidant response element (ARE) promoter regulatory sequence. Under basal conditions, in which the redox homeostasis is maintained in cells, Nrf2 is sequestered in the cytoplasm by a protein known as Keap1, which targets Nrf2 for ubiquitination and degradation by the proteasome, and thus controls both the subcellular localization and steady-state levels of Nrf2. In response to oxidative stress or chemopreventive compounds, Keap1-mediated ubiquitination of Nrf2 is decreased significantly and the Nrf2 pathway is turned on. Thus, Keap1 is a molecular switch that senses various stimuli and turns the Nrf2 pathway on and off. Administration of Nrf2-inducing agents has been shown to result in decreased carcinogenesis in animal models and altered carcinogen metabolism in humans. Clinical interventions have shown that Nrf2 inducers increase cytoprotective enzyme expression, resulting in modulation of aflatoxin disposition.

Interestingly, Nrf2 and its downstream genes are overexpressed in many cancer cell lines and human cancer tissues, giving cancer cells an advantage for survival and growth. Furthermore, Nrf2 is upregulated in resistant cancer cells and is thought to be responsible for acquired chemoresistance. Therefore, it may be necessary to inhibit the Nrf2 pathway during chemotherapy, and thereby favor the action of concomitantly administered chemotherapeutic agents.

Keap1 contains the BTB domain mediating Keap1 homodimer formation, the 'intervening region' (IVR) (amino acids 180-314), and the C-terminal Kelch domain that mediates binding to the Neh2 domain of Nrf2. Human Keap1 contains 27 cysteine residues. Three key cysteine residues (C151, C273, and C288) have been identified. C151 is required for several Nrf2 inducers, such as sulforaphane (SFN) and tert-butylhydroquinone, to manifest their effect. Importantly, residues C273 and C288 at the IVR domain are necessary for Keap1 to repress Nrf2. A single cysteine to serine mutation C273S or C288S render Keap1 unable to repress Nrf2. The transgenic expression of mutant Keap1 (C273A) and/or Keap1(C288A) protein in Keap1 null mice failed to reverse constitutive Nrf2 activation, indicating that cysteine residues at positions 273 and 288 are essential for Keap1 to repress Nrf2 activity in vivo. This suggests a critical role of the domains of Keap1 in the regulation of the functional interaction of Keap1 with Nrf2.

Therefore, there is a need for the identification of small molecules to modulate the interaction of Keap1 with Nrf2.

There is a need for the identification of small molecules to induce Nrf2 activity and stimulate or at least positively influence its activity.

There is a need for the identification of small molecules to inhibit Nrf2 activity and prevent or at least negatively influence its activity.

SUMMARY

In a first embodiment there is disclosed a modulator of Nrf2 protein comprising a compound which binds at least one of a BTB domain, an IVR domain and a Kelch domain of Keap1 protein. The modulator restores, enhances, reduces or impairs protein-protein interactions among the Keap1 protein and at least one of the Nrf2 protein and Cul3 protein, for inhibiting or activating the activity of Nrf2.

The modulator may be a compound of formula (I), (II), (III), (IV) or (V):

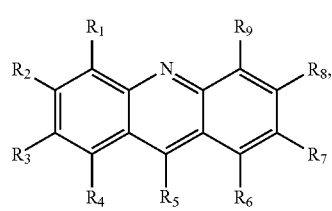

(I)

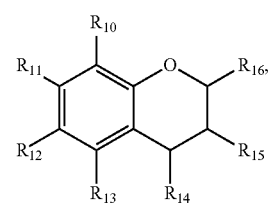

(II)

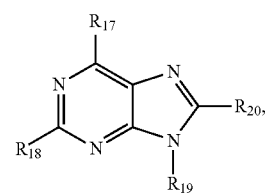

(III)

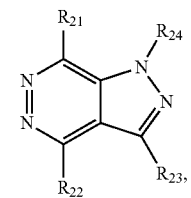

(IV)

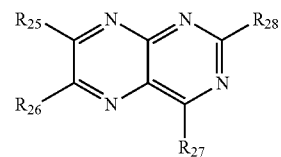

(V)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$ and $R_{28}$ may be independently chosen or identical, and may be chosen from hydrogen, halide, hydroxyl, alkyl, substituted alkyl, alkenyl, substituted alkenyl, aryl, substituted aryl, alkyloxide, substituted alkyloxide, halogenated alkyl, halogenated alkenyl, halogenated alkyloxide, halogenated substituted alkyloxide, amine, substituted amine, cycloalkyl, substituted cycloalkyl, heterocyclic aromatic or non-aromatic 5- to 10-membered ring containing 1-4 heteroatoms selected from N, O or S, wherein N and S can be oxidized and N can be quaternized, $=O$, $CH_3$, $OCH_3$, $OC_2H_5$, $NO_2$, CN, F, Cl, Br, SH, $CF_3$, $OCF_3$, $O(CF_2)_2H$, $NH_2$, $N(CH_3)_2$, $N(C_2H_4OH)_2$, $CH(OC_2H_5)_2$,

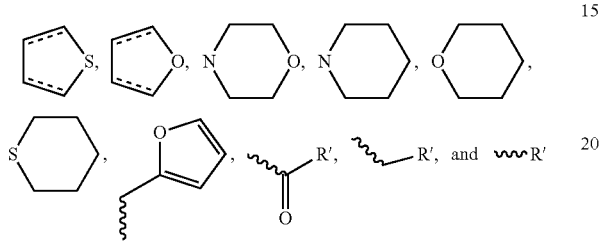

The ⌇ indicates an attachment point, and R' is chosen from hydrogen, halide, hydroxyl, alkyl, substituted alkyl, alkenyl, substituted alkenyl, aryl, substituted aryl, alkyloxide, substituted alkyloxide, halogenated alkyl, halogenated alkenyl, halogenated alkyloxide, halogenated substituted alkyloxide, amine, substituted amine, cycloalkyl, substituted cycloalkyl, heterocyclic aromatic or non-aromatic 5- to 10-membered ring containing 1-4 heteroatoms selected from N, O or S, wherein N and S can be oxidized and N can be quaternized, $=O$, $CH_3$, $OCH_3$, $OC_2H_5$, $NO_2$, CN, F, Cl, Br, SH, $CF_3$, $OCF_3$, $O(CF_2)_2H$, $NH_2$, $N(CH_3)_2$, $N(C_2H_4OH)_2$, $CH(OC_2H_5)_2$,

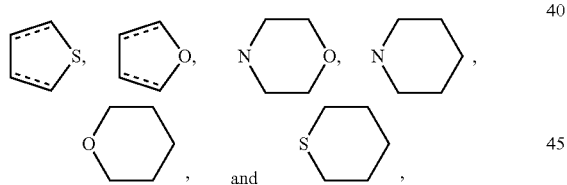

The ═ is a single bond or a double bond;

pharmaceutically acceptable salt, racemic mixture, enantiomer, diastereoisomer, isomer, and tautomer thereof.

The compound of formula (I) may be:

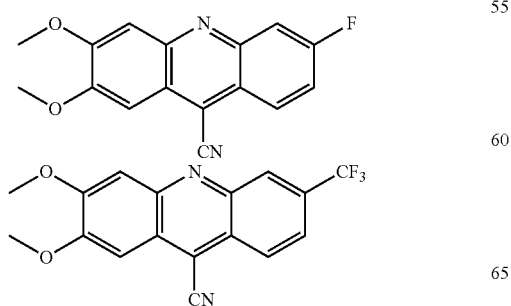

-continued

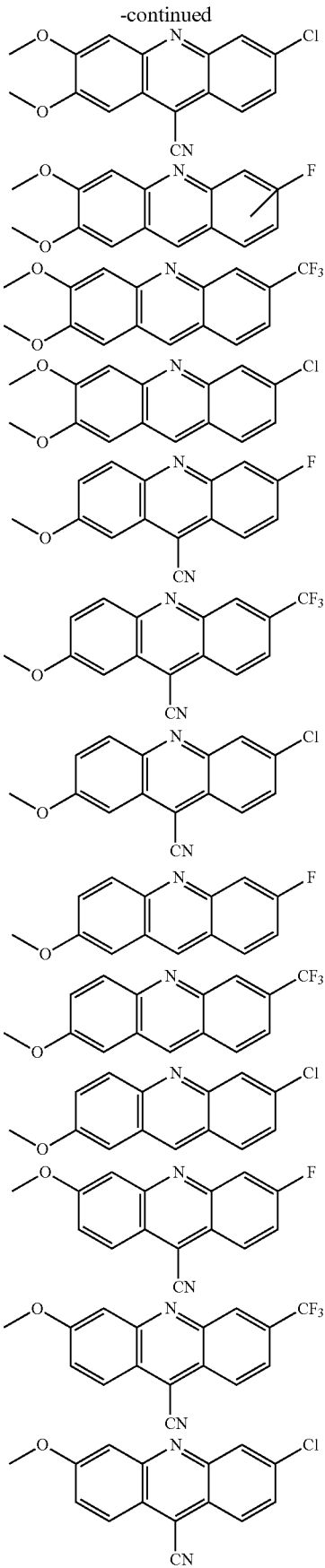

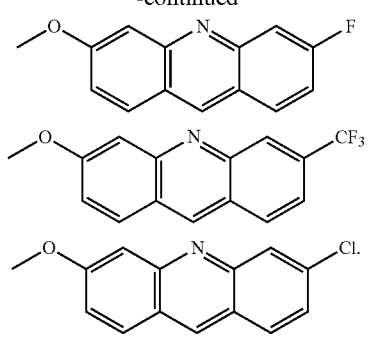
The compound of formula (II) may be:
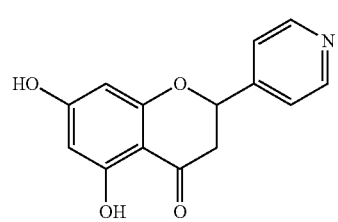
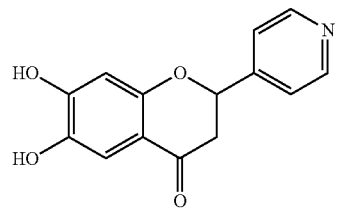
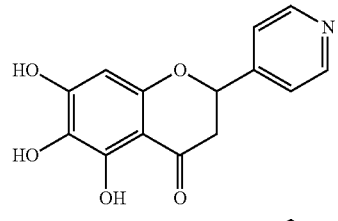
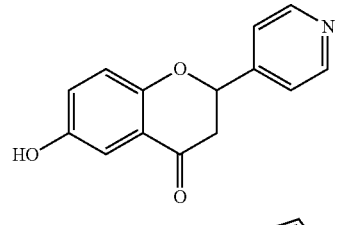
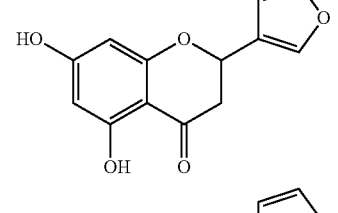
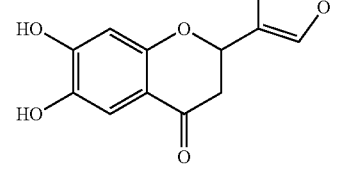
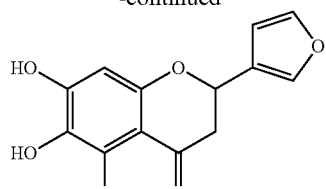
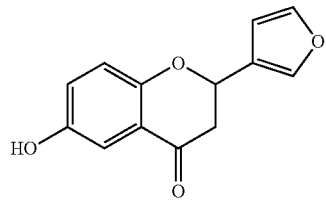
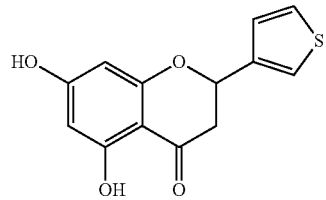
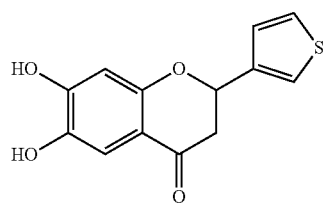
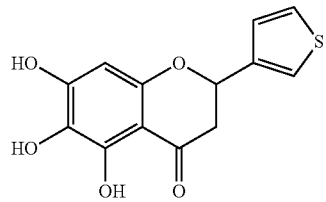
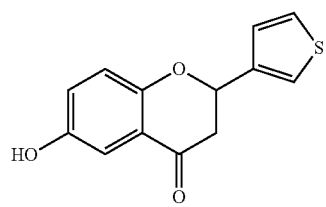
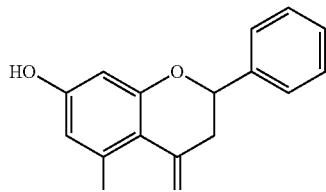
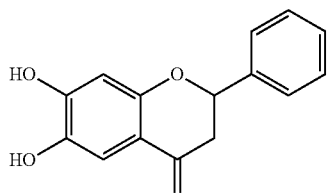

-continued
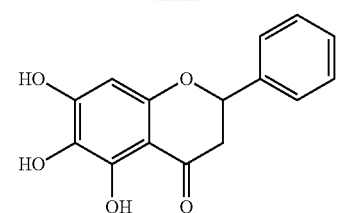
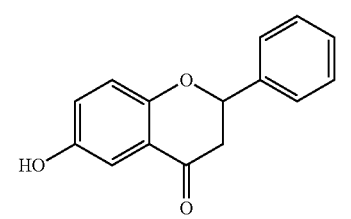
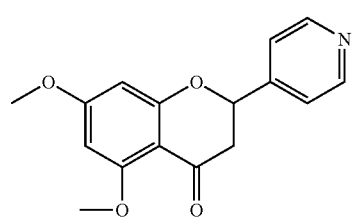
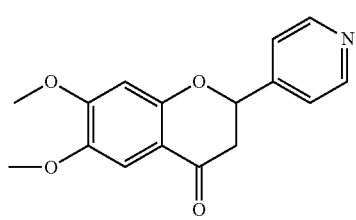
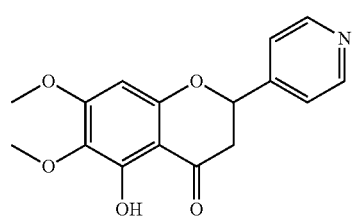
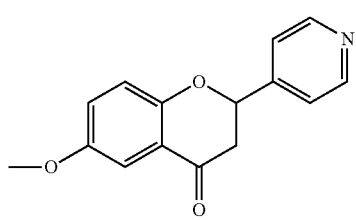
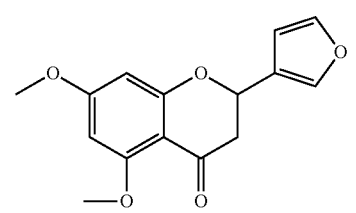
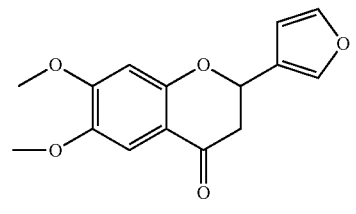
-continued
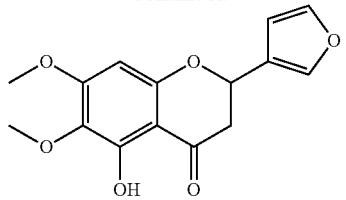
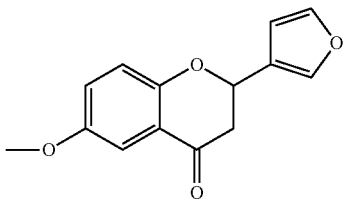
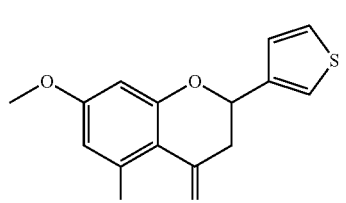
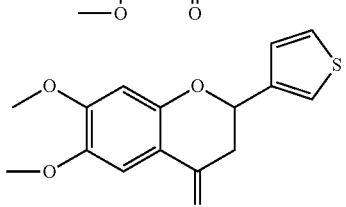
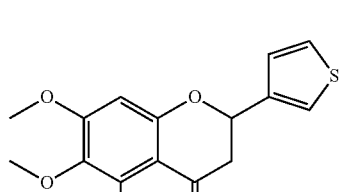
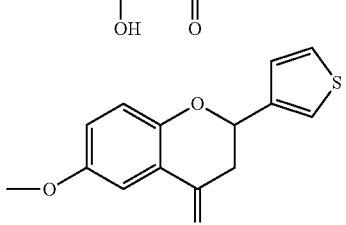
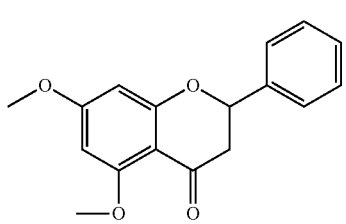
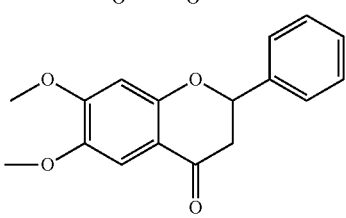

-continued
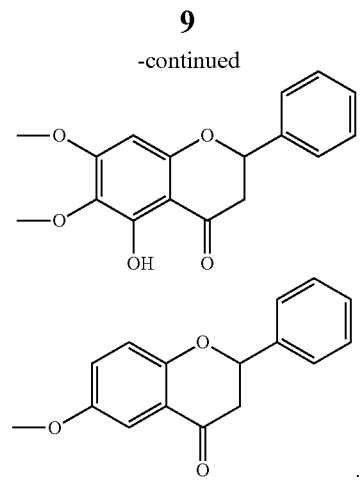
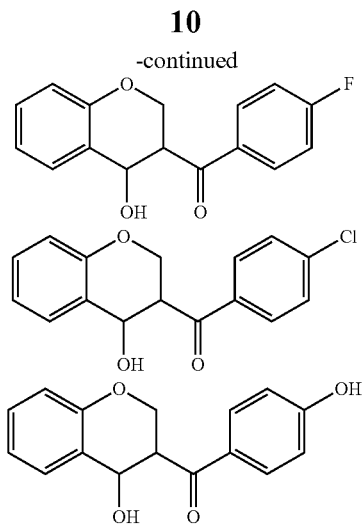
The compound of formula (II) may be:
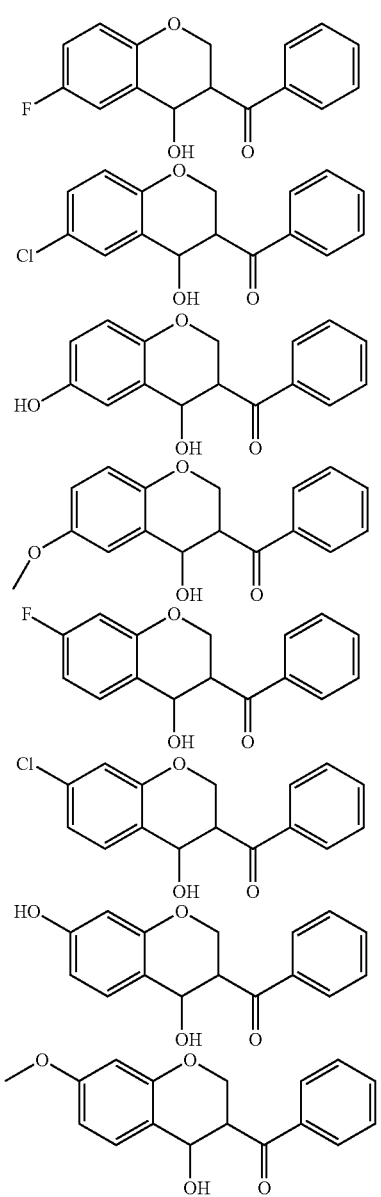
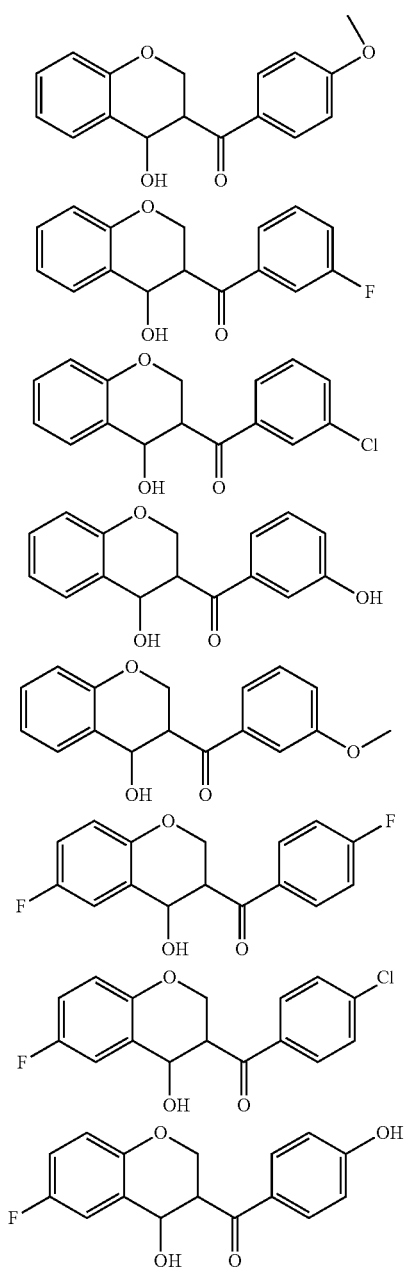

-continued
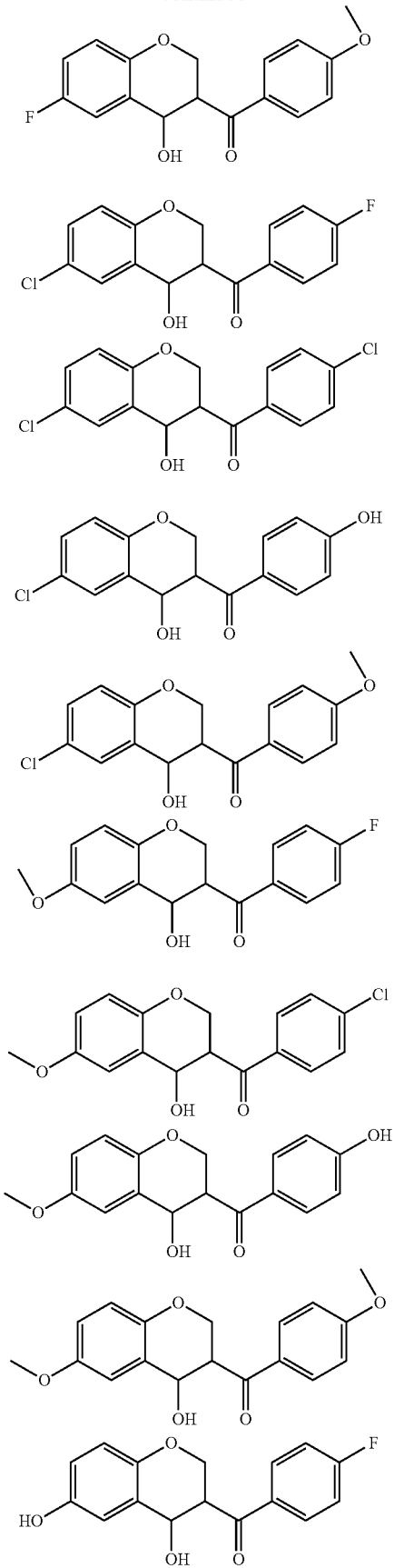
-continued
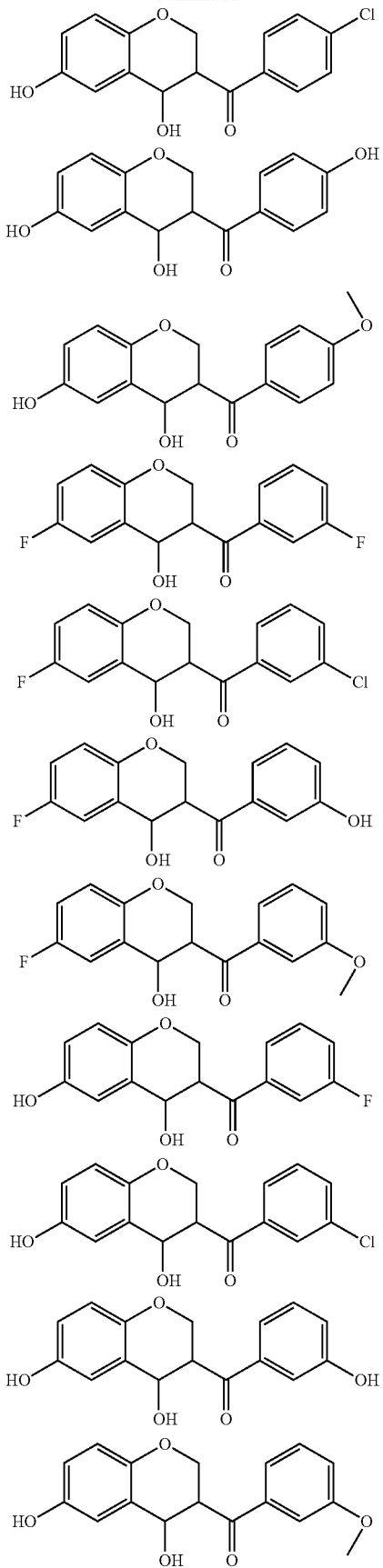

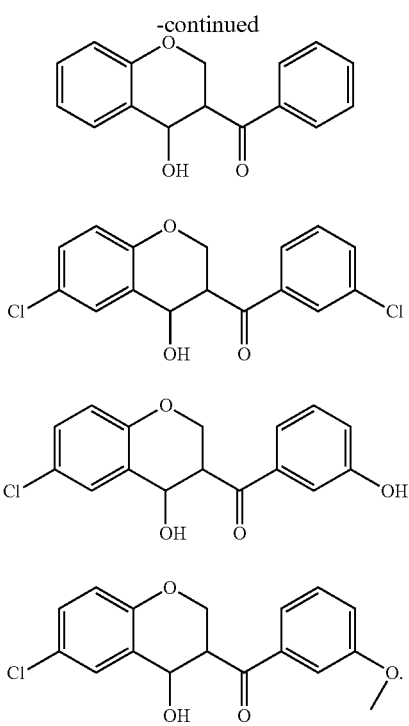
The compound of formula (III) may be:
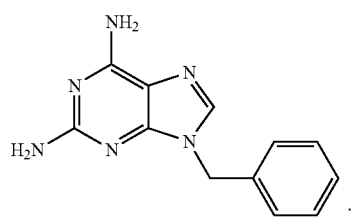 [SMILES: Nc1nc(N)c2ncn(Cc3ccccc3)c2n1]
The compound of formula (III) may be:
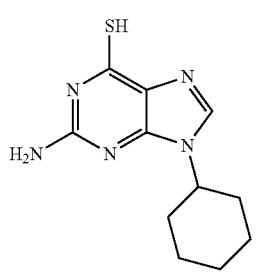
The compound of formula (III) may be:
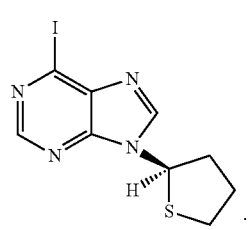 [SMILES: Ic1ncnc2c1ncn2[C@H]1CCCS1]
The compound of formula (III) may be:
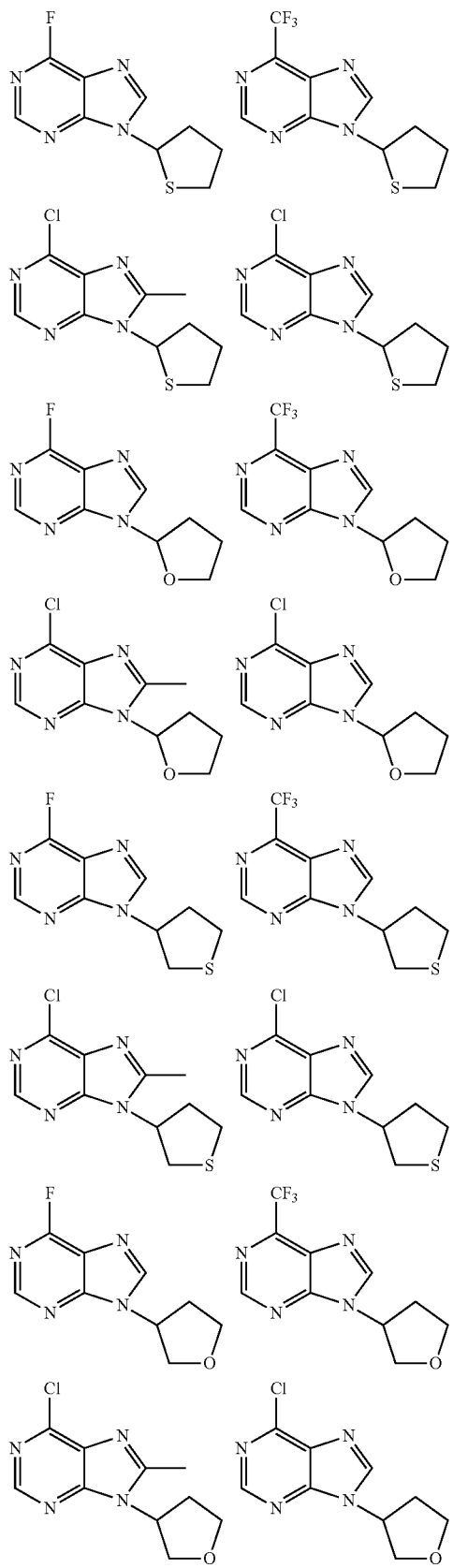

15
-continued
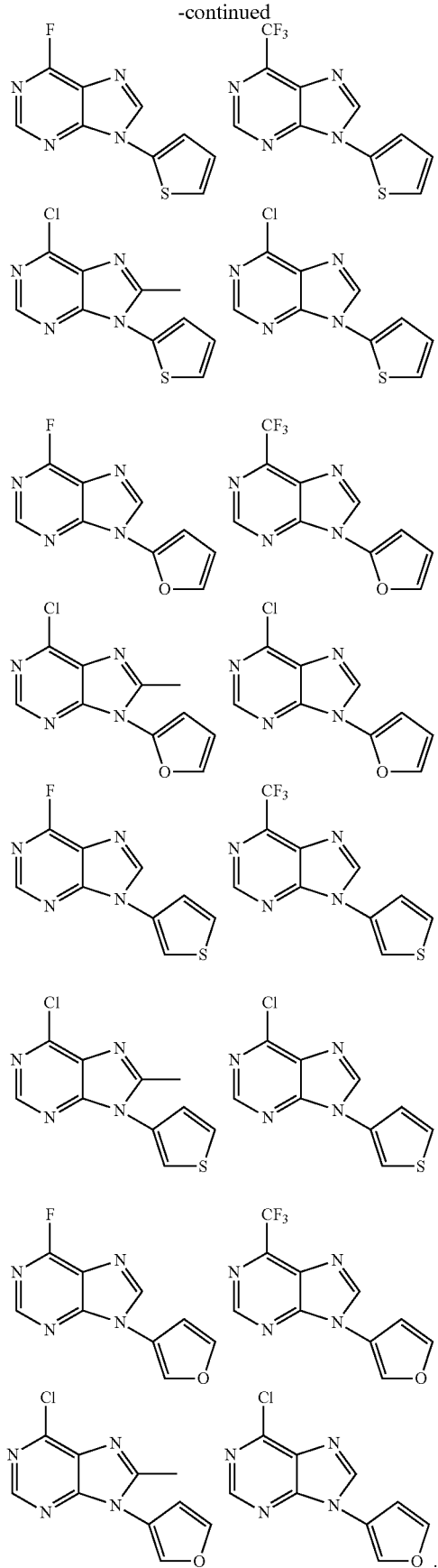
16
The compound of formula (IV) may be:
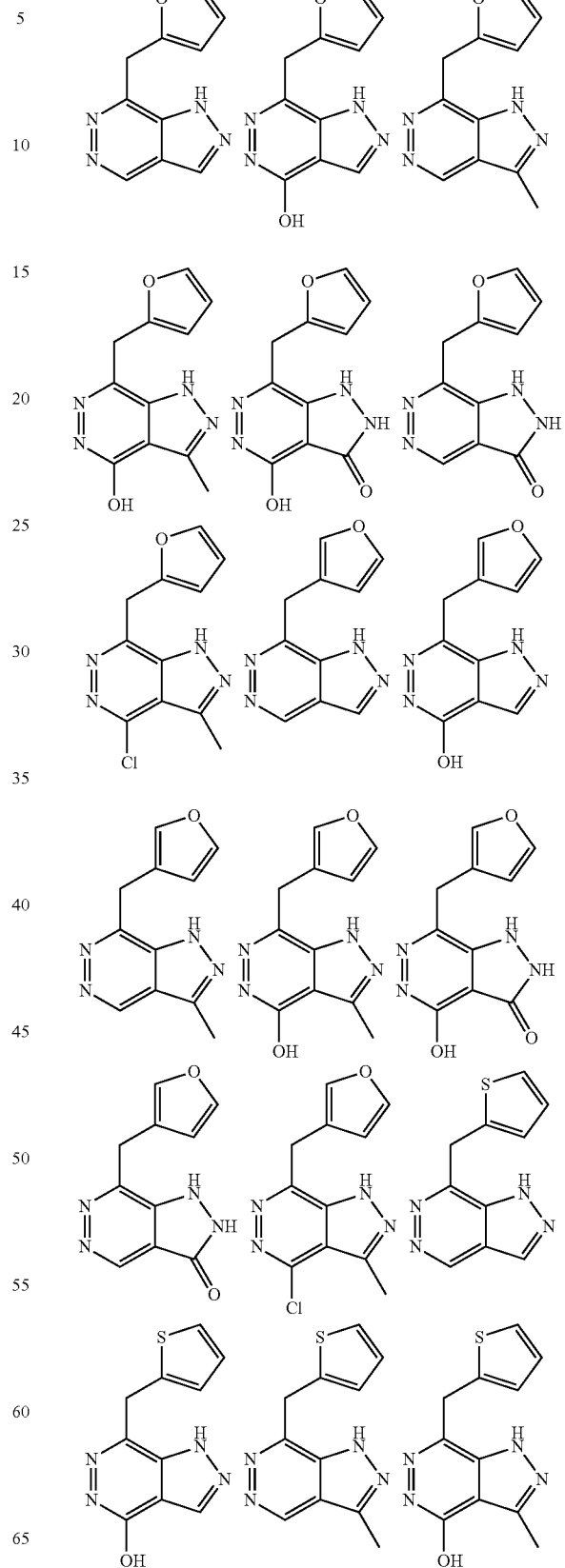

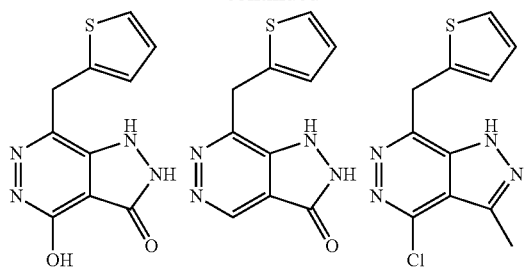
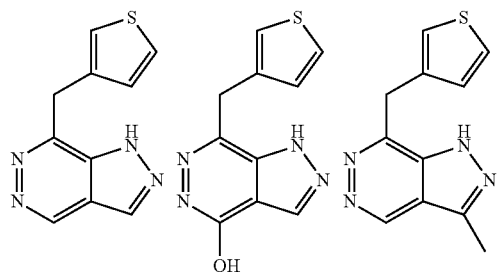
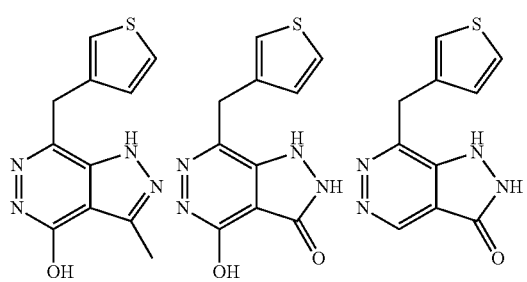
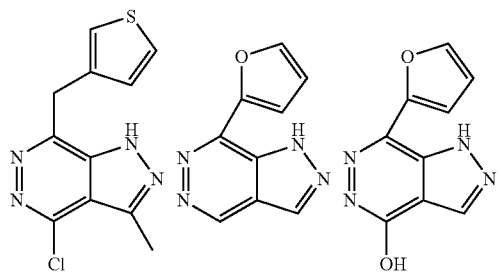
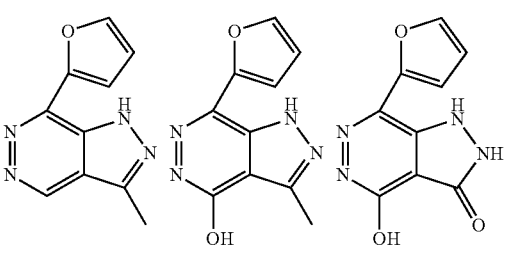
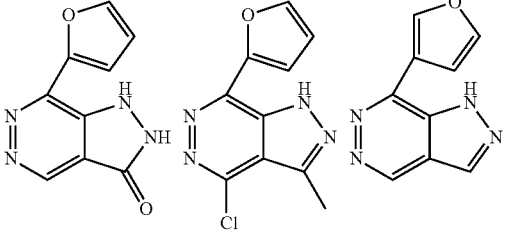
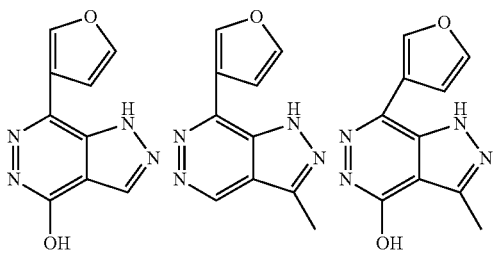
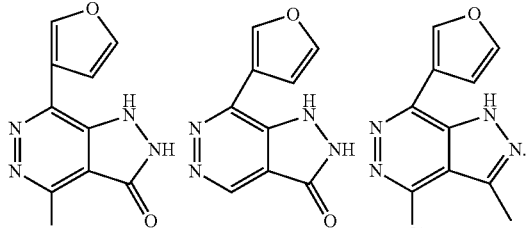
The compound of formula (IV) may be:
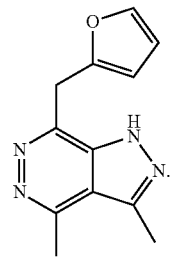 [SMILES: Cc1nnc(Cc2ccco2)c2[nH]nc(C)c12]
The compound of formula (V) may be:
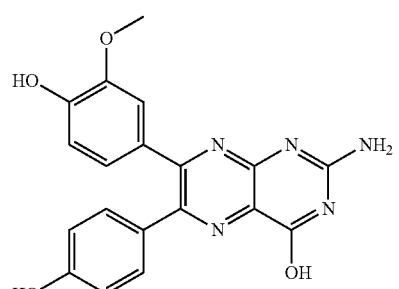
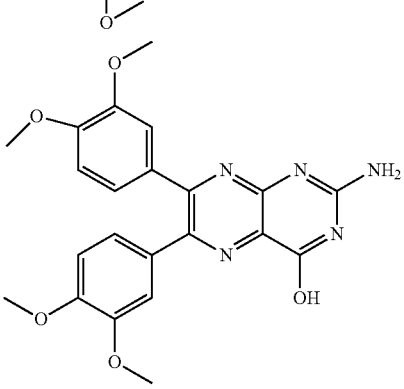

-continued
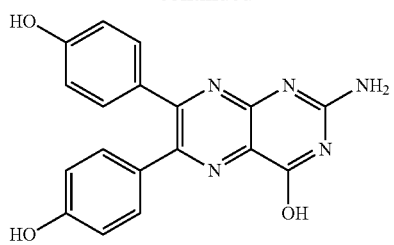
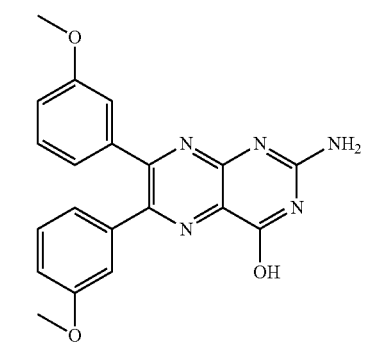
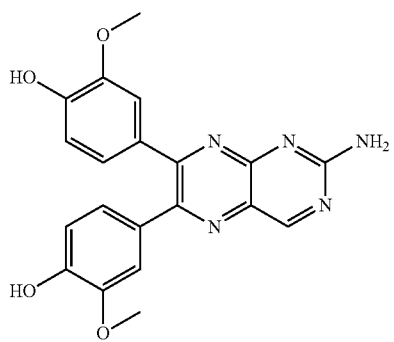
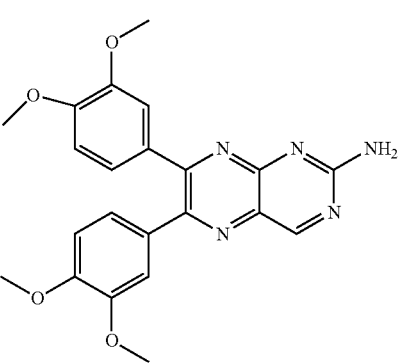
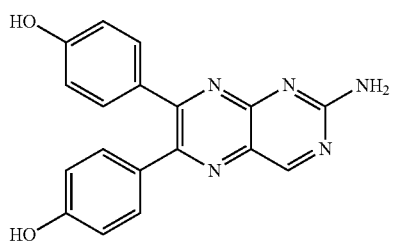
-continued
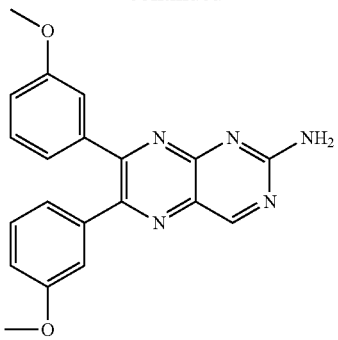
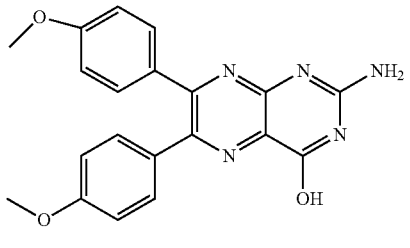
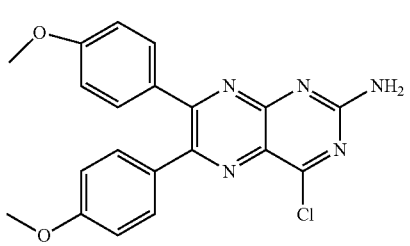
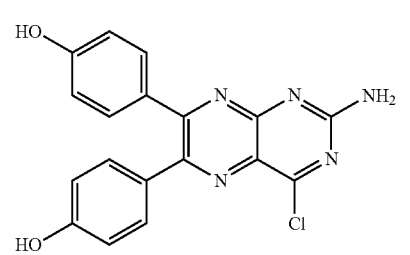
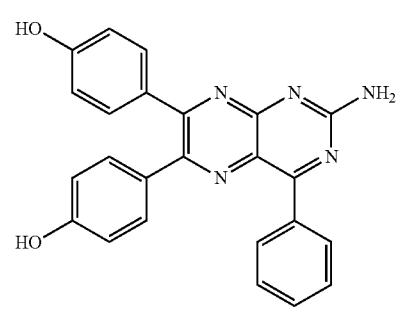
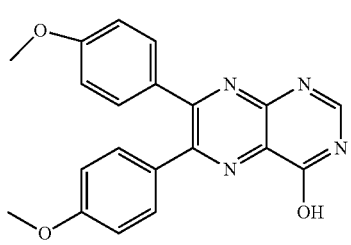

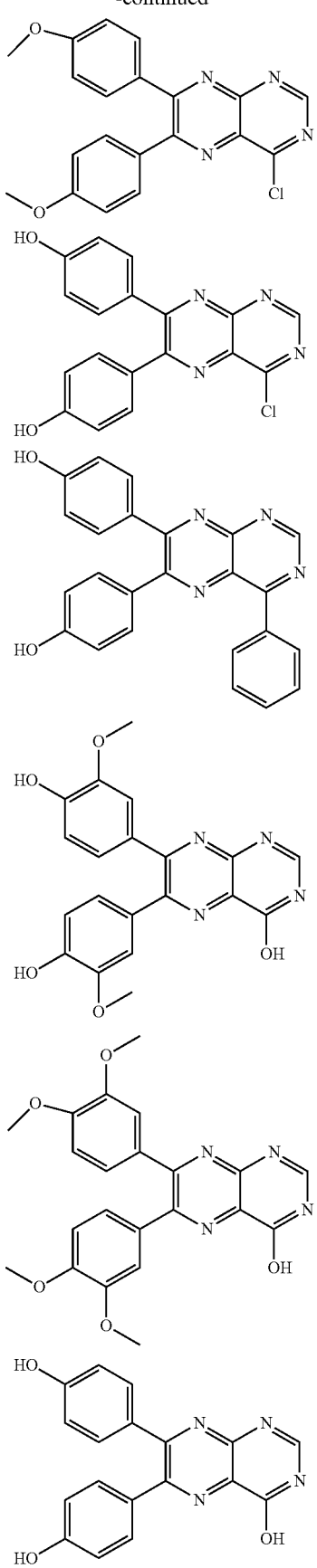

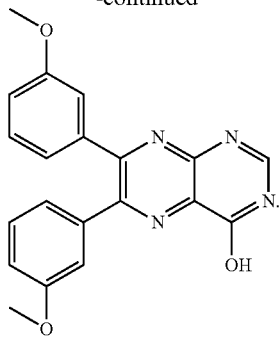

The modulator may be an inhibitor of Nrf2.

The modulator may be an activator of Nrf2.

In another embodiment, there is disclosed a pharmaceutical composition for activating Nrf2 protein which comprises a therapeutically effective amount of a modulator of the present invention, in association with a pharmaceutically acceptable carrier.

In another embodiment, there is disclosed a pharmaceutical composition for neuroprotection which comprises a therapeutically effective amount of a compound of formula (I), (II), (III), (IV) or (V) of the present invention, in association with a pharmaceutically acceptable carrier.

In yet another embodiment, there is disclosed a pharmaceutical composition for the inhibition of Nrf2 protein which comprises a therapeutically effective amount of a compound of formula (I), (II), (III), (IV) or (V) of the present invention in association with a pharmaceutically acceptable carrier.

In yet another embodiment, there is disclosed a pharmaceutical composition for overcoming drug resistance in cancer chemotherapy, and for the inhibition of tumor growth which comprises a therapeutically effective amount of a compound of formula (I), (II), (III), (IV) or (V) of the present invention, in association with a pharmaceutically acceptable carrier.

In another embodiment, there is disclosed a use of a compound of formula (I), (II), (III), (IV) or (V) of the present invention, for the treatment or prevention of a condition which involves the abnormal activity and/or expression level of Nrf2 protein.

The condition may be an oxidative stress associated disease.

The oxidative stress associated disease may be Parkinson's disease, Parkinson's disease with dementia with Lewy body, Huntington's disease, multiple system atrophy (MSA), progressive supranuclear palsy (PSA), corticobasal degeneration (CBD), and frontotemporal lobe degeneration.

The oxidative stress associated disease may be atherosclerosis, heart failure, myocardial infarction, Alzheimer's disease, Fragile X syndrome, and chronic fatigue.

The condition may be a cancer.

The cancer may be liver cancer, lung cancer, breast cancer, prostate cancer, colon cancer, neuroblastoma or leukemia.

In another embodiment, there is disclosed a use of a compound of formula (I), (II), (III), (IV) or (V) of the present invention, for the fabrication of a medicament for treatment or prevention of a condition which involves the abnormal activity and/or expression level of Nrf2 protein.

In yet another embodiment, there is disclosed a method for effecting neuroprotection in a patient in need thereof by administering a therapeutically effective amount of a compound of formula (I), (II), (III), (IV) or (V) of the present invention.

In another embodiment, there is disclosed a method for treating a disease which involves the abnormal activation and or expression level of a Nrf2 protein in a patient in need thereof by administering a therapeutically effective amount of a compound of formula (I), (II), (III), (IV) or (V) of the present invention.

In another embodiment, there is disclosed a method for treating a disease which involves at least one of 1) the abnormal activation and or expression level of a Nrf2 protein, and 2) the abnormal inhibition of a Nrf2 protein, by administering a therapeutically effective amount of a compound of formula (I), (II), (III), (IV) or (V) of the present invention.

The disease may be an oxidative stress associated disease chosen from Parkinson's disease, Parkinson's disease with dementia with Lewy body, Huntington's disease, multiple system atrophy (MSA), progressive supranuclear palsy (PSA), corticobasal degeneration (CBD), and frontotemporal lobe degeneration.

The disease may be an oxidative stress associated disease chosen from atherosclerosis, heart failure, myocardial infarction, Alzheimer's disease, Fragile X syndrome, and chronic fatigue.

In another embodiment, there is disclosed a method for treating a cancer in a subject in need thereof by administering a therapeutically effective amount of a compound of formula (I), (II), (III), (IV) or (V) of the present invention.

In yet another embodiment, there is disclosed a method of preventing a cancer in a subject in need thereof by administering a therapeutically effective amount of a compound of formula (I), (II), (III), (IV) or (V) of the present invention.

The cancer may be liver cancer, lung cancer, breast cancer, prostate cancer, colon cancer, neuroblastoma or leukemia.

The following terms are defined below.

The term "oxidative stress" is intended to mean an imbalance between the production of reactive oxygen species and a biological system's ability to readily detoxify the reactive intermediates or easily repair the resulting damage. All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids, and DNA.

The term "modulator" is intended to mean a means to regulate, adjust or adapt the activity of a given target (e.g. Nrf2). Modulation may be of varying intensity and may range from weak to strong. The modulator may be inhibitory (preventing the activity of the target) or stimulatory (inducing the activity of the target).

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

FIG. 10 illustrates the sequence of Full length sequence of human Keap1 (1-624) (SEQ ID NO:1), the BTB domain (amino acids 67-170) of human Keap1 (SEQ ID NO:2), the IVR domain (amino acids 180-314) of human Keap1 (SEQ ID NO:3), and the Kelch domain (amino acids 315-598) of human Keap1 (SEQ ID NO:4).

DETAILED DESCRIPTION OF THE PREFERRED EMBODIMENTS

In embodiments there are disclosed modulators of the interaction between Nrf2 protein and Keap1 protein. The modulators may comprises a compound which binds at least one of the BTB domain (amino acids 67-170) (SEQ ID NO:2), an IVR domain (amino acids 180-314) (SEQ ID NO:3) and Kelch domain (amino acids 315-598) of the Keap1 protein (SEQ ID NO:4).

The present invention combines in silico screening with cell based assays to identify novel agents that modulate the Keap1-Nrf2 signalling pathway. A three-dimensional (3D) structural model of the Keap1 IVR domain was built and utilized to virtually screen the chemical databases for putative Nrf2 modulators, which were subsequently tested by luciferase-based reporter gene assays and/or Western blot analyses.

The modulators may modulate the interaction of Keap1 with Nrf2 to prevent keap1 from binding to Nrf2, hence stimulating the activity of Nrf2, or they may modulate the interaction between Keap1 and Cul3, and reduce Nrf2 degradation, hence stimulating the activity and/or expression level of Nrf2. On the other hand, they may favor the interaction of Keap1 with Nrf2, hence preventing the release of Nrf2 from keap1. In addition, they may restore the association of Keap1 and Nrf2 that is weakened or lost due to mutations at Keap1, Nrf2 or both of them.

The modulators of the present invention may be useful for the treatment of conditions in which the activity of Nrf2 is misregulated or detrimental to a biological or treatment process. Nrf2 is an important molecular switch for activating genes important in the cellular adaptation to redox stress. Modulators stimulating the activity of Nrf2 may therefore be useful for the treatment conditions in which this adaptation is reduced, disrupted or absent and reestablishment of a response to oxidative stress is required. Several human conditions have been linked to such disruption. These include Parkinson's disease, Parkinson's disease with dementia with Lewy body, as well as other related diseases, such as multiple system atrophy (MSA), progressive supranuclear palsy (PSA), corticobasal degeneration (CBD), frontotemporal lobe degeneration and huntington's disease. Other diseases in which oxidative stress is involved include but are not limited to atherosclerosis, heart failure, myocardial infarction, Alzheimer's disease, Fragile X syndrome, and chronic fatigue.

The modulators of the present invention may be seen as playing a protective role (i.e. neuroprotective, cardioprotective, etc) by at least slowing, if not preventing the progress of neurodegenerative or cardiac diseases. In addition, the modulators of the present invention may act as cancer chemoprevention agents.

Figure 7:
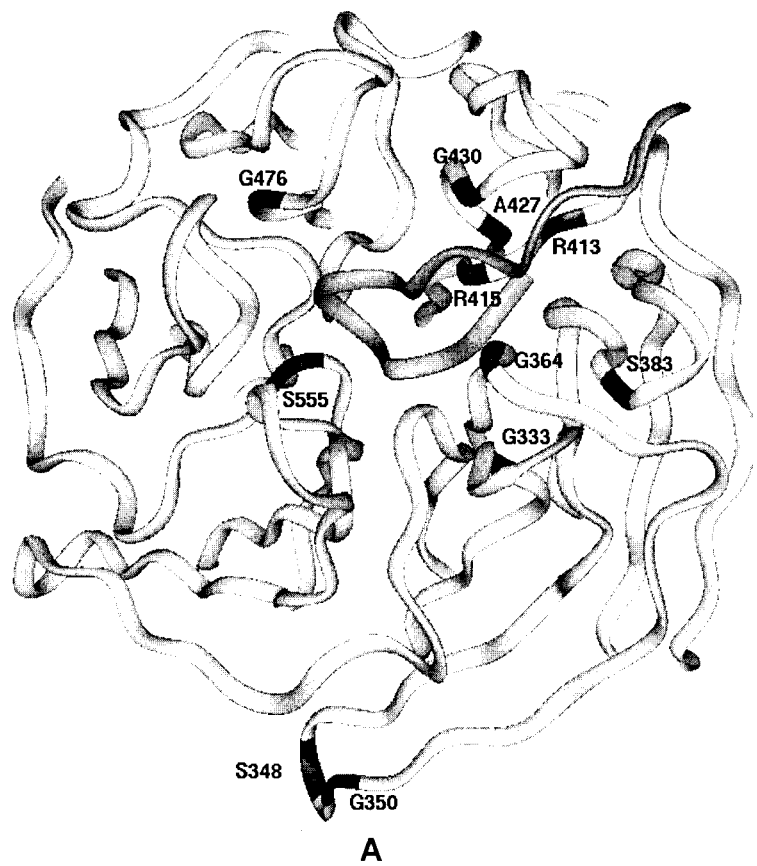
FIG. 7 illustrates ribbon representation (A) and molecular surface (B) of the crystal structure of Keap1 Kelch domain (ribbon in white and red) in complex with Nrf2-derived peptide (ribbon in cyan) where the mutation distribution at Keap1 Kelch domain are labeled and shown in red ribbon.
Figure 7:
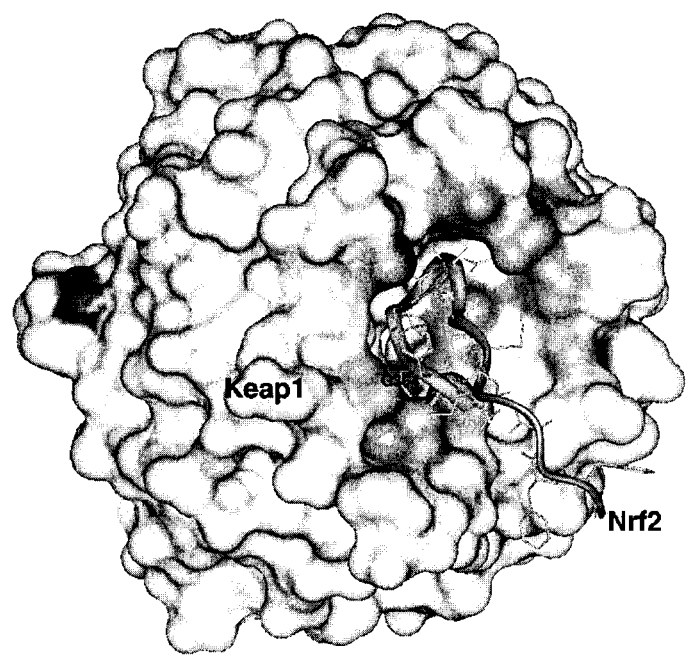

The modulators of the present invention may inhibit the activity of Nrf2. The modulator may prevent the release of Nrf2 from Keap1 and/or stimulate its degradation. Multiple Keap1 and Nrf2 mutations have been identified in cancers. These mutations affect the interaction of Keap1 with Nrf2 by interfering with the repressive activity of Keap1 toward Nrf2. Therefore, the modulator of the present invention may be useful for the treatment of conditions in which the repressive activity of Keap1 towards Nrf2 is weakened or impaired due to mutations in Keap1, Nrf2 or both of them. Examples of mutations of Keap1 include, but not limit to, S104A, H200P, D236H, C273A, R272c, Q284L, C288A, T314M, G333S, G350S, G364C, G379D, R413L, R415G, A427V, and G430C. Selected mutations are indicated in FIG. 7. The mutations at the BTB domain and IVR region may affect the Keap1/Cul3 interaction as well as the Keap1/Nrf2 interaction.

Such conditions include but are not limited to cancers. The cancers include but are not limited to liver cancer, lung cancer, breast cancer, prostate cancer, colon cancer, neuroblastoma or leukemia. In such conditions, the reduction in or the inability of Keap1 of repressing Nrf2 (which may or may not be caused by mutations) results in increased Nrf2 activity. This increased activity over-stimulates the cellular Nrf2-dependent response, and cause tumor cells to become resistant to drugs with which they are treatment. Thus, tumor cells could hijack the Nrf2 pathway to their survival advantage, conferring resistance to chemotherapeutic agents. The Nrf2 modulators of the present invention are useful for overcoming drug resistance in cancer chemotherapies, and they are also useful for inhibiting tumor growth since tumor cells may depend on aberrant activation of Nrf2.

Novel Nrf2 modulators are identified, BM4, BM5, BM6, BM9, BM10, BM18, BM19, BM31 and BM40 that triggered Nrf2 nuclear translocation. (Scheme 1) It is demonstrated that BM10, BM31, and BM40 triggered Nrf2 nuclear translocation and induced expression of ARE-regulated enzymes, such as γ-glutamylcysteine synthetase (GCS). The present invention includes BM31 that in the low dose range (50-200 nM) provides protections for the MCF-7 cells from cytotoxic damage of carcinogen benzo[a]pyrene (B[a]P).

Alternative Embodiments—Part A

Construction of the 3D Model of Keap1 IVR and Virtual Screening

Figure 1:
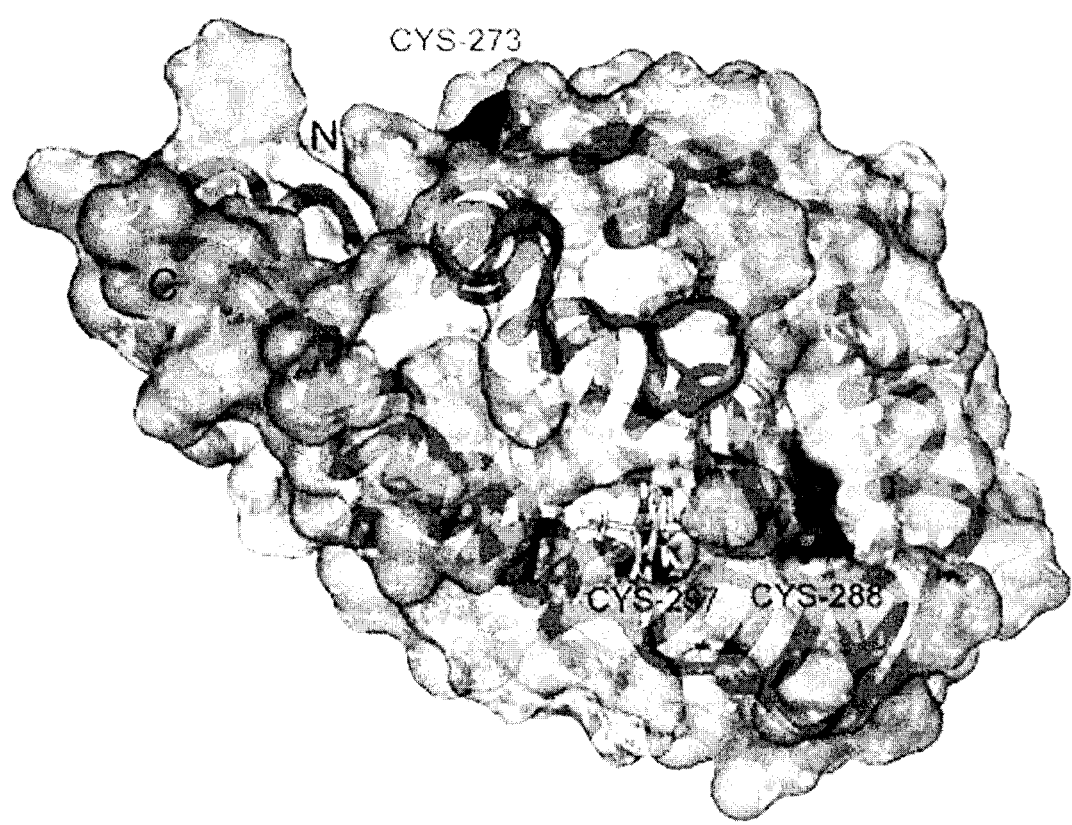
FIG. 1 illustrates a structural model of the intervening region (IVR, amino acids 180-314) of human Keap1 according to the present invention.

Using a novel fold recognition technique as implemented in program Prospect (Oak Ridge National Laboratory, Oak Ridge, Tenn., USA), the crystal structure of FadR (PDB entry: 1e2x), a fatty acid-responsive transcription factor is identified as a structure template for the construction of the 3D model of Keap1 IVR (residues 180-314). The percentage of the sequence identify and strong similarity between Keap1 IVR (residues 180-314) and the template (1e2x, residues 25-225) is 33.65%. Based on this template, 100 structural models of Keap1 IVR are generated using software MODELLER v8 (9) and the model with lowest objective function is selected for further study. As shown in FIG. 1, residues Cys-297 and CYS-288 (red surface) are inside the cavities, whereas Cys-273 (red surface) and Cys-257 (on the other side of the surface) are on the surface but not inside a cavity. Ethoxyquin (in green sticks) was docked into the surface cavity that includes Cys-297.

Docking of ethoxyquin (EQ) and virtual screening of chemical database are performed using software GOLD v3.0 (The Cambridge Crystallographic Data Centre, Cambridge, UK). The ligand is treated as fully flexible whereas the protein is kept rigid except that each serine, threonine, and tyrosine hydroxyl group are allowed to rotate to optimize hydrogen bonding. The scoring function GoldScore and the GOLD standard default parameter setting were selected.

Cell Culture

The HepG2, MCF-7, and 293T cell lines are purchased from the American Type Culture Collection (ATCC; Manassas, Va., USA). The HepG2 cells are grown in alpha-minimal essential media supplemented with non-essential amino acids, sodium pyruvate, 90% Earle's balanced salt solution, and 10% fetal bovine serum. MCF-7 cells are maintained in RPMI-1640 medium. The 293T cells are grown in DMEM supplemented with 10% fetal bovine serum.

Luciferase Assay

One representative ARE (A2-ARE) from GSTA2 is used in this work, and A2-ARE are cloned into the KpnI and MluI sites of pGL3-promoter vector, which contains a heterologous SV40 promoter and a firefly luciferase reporter gene. Cells are seeded at $1 \times 10^5$ per well using 24-well plate, grown overnight before being transfected transfected with pGL3 and other designated constructs using LipofectAMINE (Invitrogen) for 5 h. The plasmid pRL, containing a *renilla reniformis* luciferase reporter gene, is cotransfected as internal control to correct transfection efficiency. After transfection, cells are treated with test compounds at designated concentrations for 24 h prior to harvesting. The cells are then washed twice with phosphate-buffered saline and harvested in 100 uL of 1× passive lysis buffer (Promega, Madison, Wis., USA). The luciferase activities are analyzed in 20-uL cell extracts with the Dual luciferase Assay™ kit (Promega) on a Lumat LB 9507 luminometer (Berthold Technologies, Oak Ridge, Tenn., USA). The related luciferase activities are expressed as a ratio of the pGL3 reporter activity to that of the control plasmid pRL. The fold of induction is expressed as ratio of induction from the treated cells versus the untreated. Values represent measurements from three independent experiments performed in triplicate and are presented as the mean±SEM.

Western Blot Analysis

Cells are treated with test compounds at designated concentrations and are harvested at 24 h. Sixty microgram of cell-lysate protein and 35 ug of nuclear extract are loaded into each lane, and electrophoresed through a 4-20% gradient SDS-PAGE gel (Bio-Rad, Mississauga, ON, Canada), and transferred onto a nitrocellulose membrane. The membrane is incubated with primary antibody and subsequently incubated with HRP-conjugated secondary antibody. Finally, ECL detection is carried out, and the results were recorded on X-ray film by autophotography.

Cell Viability and Capability of Compounds in Protecting Cells from Carcinogen

Cells are seeded at $4 \times 10^3$ per well using 96-well plate, grown overnight before being treated with test compounds for 72 h. Viable cells are measured by MTT assays. To evaluate the ability of test compounds in protecting MCF-7 cells from the damage of B[a]P, MCF-7 cells are seeded at $2 \times 10^3$ per well using 96-well plate, grown overnight before being treated with test compounds at designed concentration for 48 h. Next, cells are treated with 160 nM B[a]P in the presence of test compound for another 72 h. The viable cells are measured using MTT assays. Experiments are performed in triplicate and repeated twice.

Statistical Analysis

GRAPHPAD PRISM 5 software (San Diego, Calif., USA) is used to perform statistical analysis by t-test. $p<0.05$ is considered statistical significant.

Structural Model of Keap1 IVR Domain and Virtual Screening

Residues C257, C273, C288, and C297, all of which are in IVR region, have been proposed as the direct sensors of inducers of the ARE-regulated enzymes. According to the 3D IVR model, residues C288 and C297 are found to be inside surface cavities whereas C273 and C257 are on the surface, but they are not inside a cavity (FIG. 1). The Keap1 IVR model suggested residues C297 and C288 as two possible direct sensors of Nrf2 inducers. EQ, an effective inducer of ARE-regulated enzymes, is docked into the IVR structural model. Without any preset preference between cavities C288 and C297, EQ is docked into cavity C297 automatically using software GOLD, probably because of the fact that the cavity around C288 is shallow.

Next, the Keap1 IVR/EQ complex is employed to virtually screen 90 000 compounds extracted from the NCI-3D chemical database (NCl, US) for putative Nrf2 inducers. The chemical structures and the predicted binding modes for each of the 50 top-score compounds are visually inspected. A multiple-cycle screening strategy is used. In the first cycle, chemical samples for 23 top-score compounds are obtained. Of the 23 compounds, seven hits are identified using ARE-driven luciferase assays. In the second cycle, the NCl-3D database for the analogues of the initial hits by a ligand-based approach using the tanimoto index (with a cutoff of 0.9) is screened. Chemical samples of 17 analogues are obtained of the hits from the first cycle and then they are subjected to cell-based assays. The two cycles of screenings identify 9 novel Nrf2 inducers (Scheme 1 below).

Scheme 1. 9 novel Nrf2 inducers

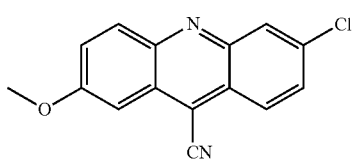
BM4

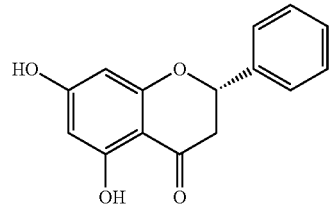
BM5

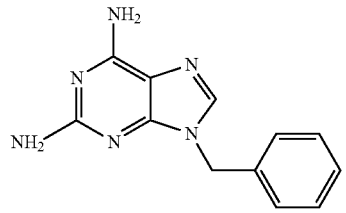
BM6

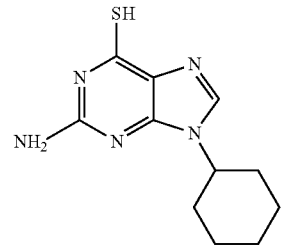
BM9

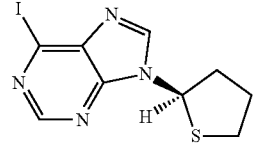
BM10

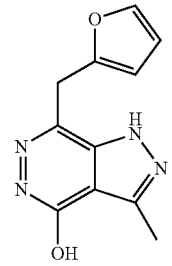
BM18

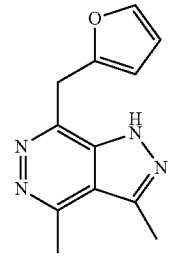
BM19

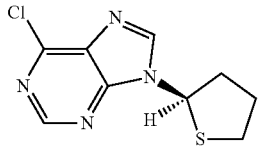
BM31

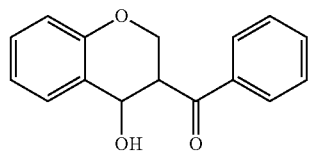 [SMILES: O=C(c1ccccc1)C1COc2ccccc2C1O]

BM40

Figure 2:
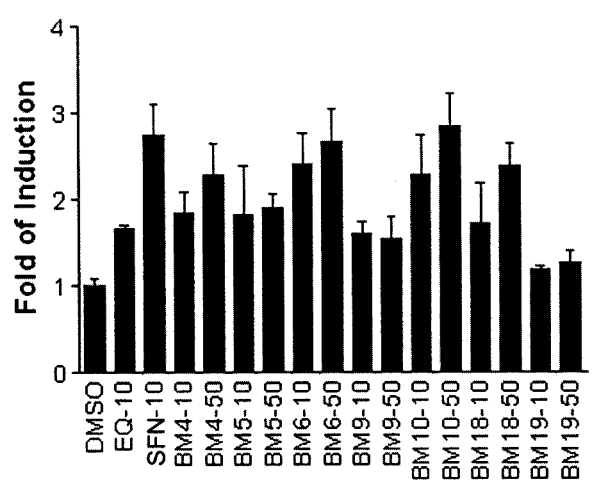
FIG. 2 illustrates the ARE-driven luciferase activity in the cell-based system exposed to the DMSO vehicle, ethoxyquin (EQ) at 10 µM, sulforaphane (SFN) at 10 and compounds BM4, 5, 6, 9, 10, 18 and 19 at 10 and 50 µM according to the present invention.
Figure 3:
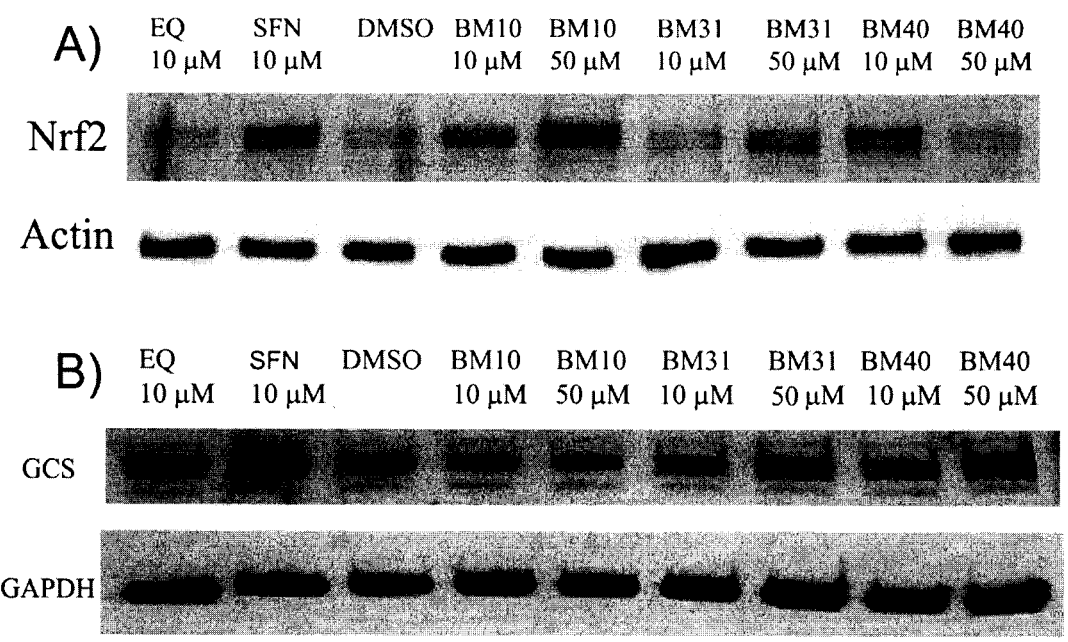
FIG. 3A illustrates Nrf2 protein detected in nuclear proteins by Western blotting.
FIG. 3B illustrates endogenous γ-glutamylcysteine synthetase (GCS), a Nrf2-regulated protein, in whole cell protein extracts, detected by Western blotting. HepG2 cells were treated with EQ, SFN, DMSO, BM10, BM31 and BM40 at designated concentrations for 24 h.
Figure 8:
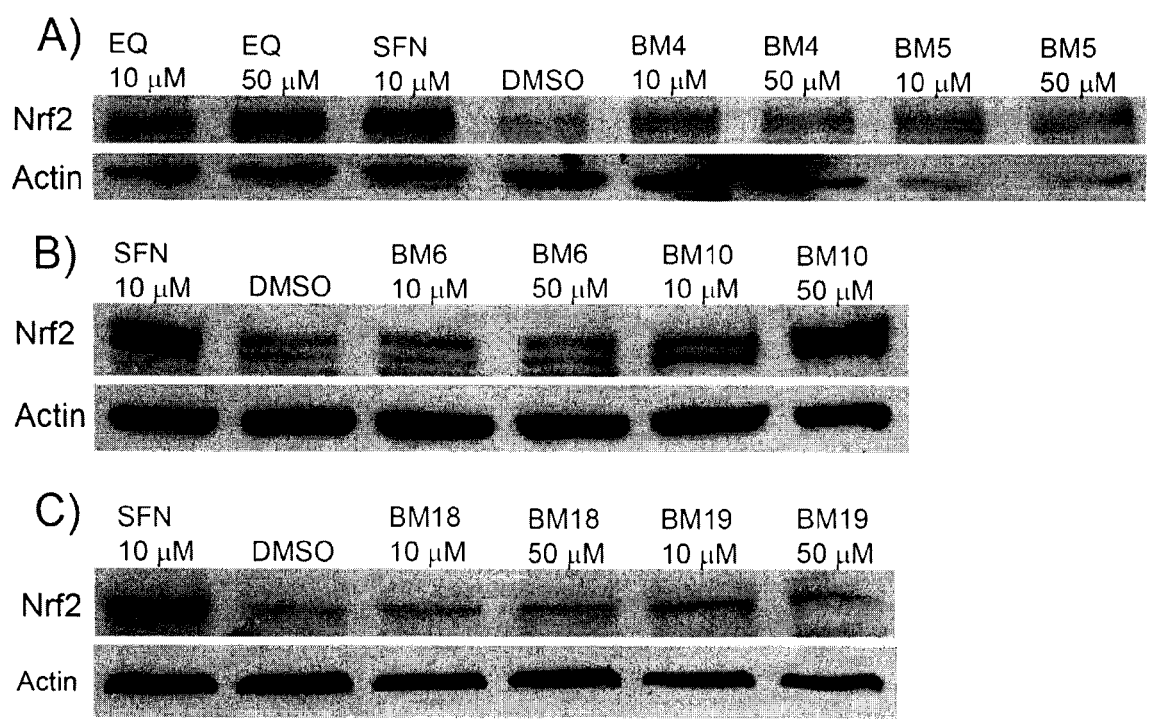
FIG. 8 illustrates Nrf2 protein detected in nuclear proteins by Western blotting (A, B, C). HepG2 cells were treated with EQ, SFN, DMSO, BM compounds at designated concentrations for 24 h. BM9 at 50 µM has modest activity in inducing Nrf2 nuclear translocation in HepG2 cells.

ARE-Driven Luciferase Assays and Western Blot Analyses of the Top-Score Compounds have Identified Novel Nrf2 Inducers The 23 top-score molecules from the first round of virtual screening are initially tested in the cell-based ARE-driven luciferase assay. Specifically, HepG2 cell line are transfected with ARE-driven pGL3 luciferase vector and then exposed to individual test compounds at 10, 50 µM. Classical Nrf2 inducers EQ and SFN were used as the positive controls. Our results showed that 7 out of 23 top-score compounds are significantly active in inducing ARE-driven luciferase activities (FIG. 3). To examine the effect of these active compounds on Nrf2 nuclear translocation, Western blot analysis is used to measure the nuclear level of Nrf2 after cells are exposed to these compounds. Among the 7 hits, compound BM10 is most potent in inducing Nrf2 nuclear translocation (FIG. 8). However, although compounds BM4, BM6, and BM18 potently induce ARE-driven luciferase activities (FIG. 2), it is found they only have modest activity in inducing Nrf2 nuclear translocation (FIG. 8), suggesting the Western blot analysis of Nrf2 nuclear translocation is a more reliable approach to detect Nrf2 inducers. Consequently, the 17 compounds from the second cycle of screening are directly subjected to Western blot analysis, which leads to identification of BM31 and BM40 as potent Nrf2 inducers. Overall, our results show BM10, BM31, and BM40 potently elevate the nuclear Nrf2 in HepG2 cells, and their potencies are comparable to that of SFN (FIG. 3A).

Compounds BM10, 31 and 40 Induce Downstream Carcinogen-Detoxifying Enzymes

Nrf2 is a master transcription factor regulating multiple ARE-regulated antioxidant and detoxifying enzymes, such as GCS, glutathione S-transferase (GST), NAD(P)H quinone oxidoreductase-1 (NQO1), and UDP glucuronosyltransferase (UGT), etc. The effects of our lead compounds on GCS are examined. Our results demonstrate that GCS was indeed induced by BM10, 31, 40 (FIG. 3B). The potencies of BM31 and BM40 are comparable to that of SFN and EQ. It is of note that despite BM10 potently inducing nuclear translocation of Nrf2, it shows modest potency in inducing the GCS.

Impact of Keap1 Mutation on the Nrf2-Inducing Potency of BM31 and SFN

Figure 4:
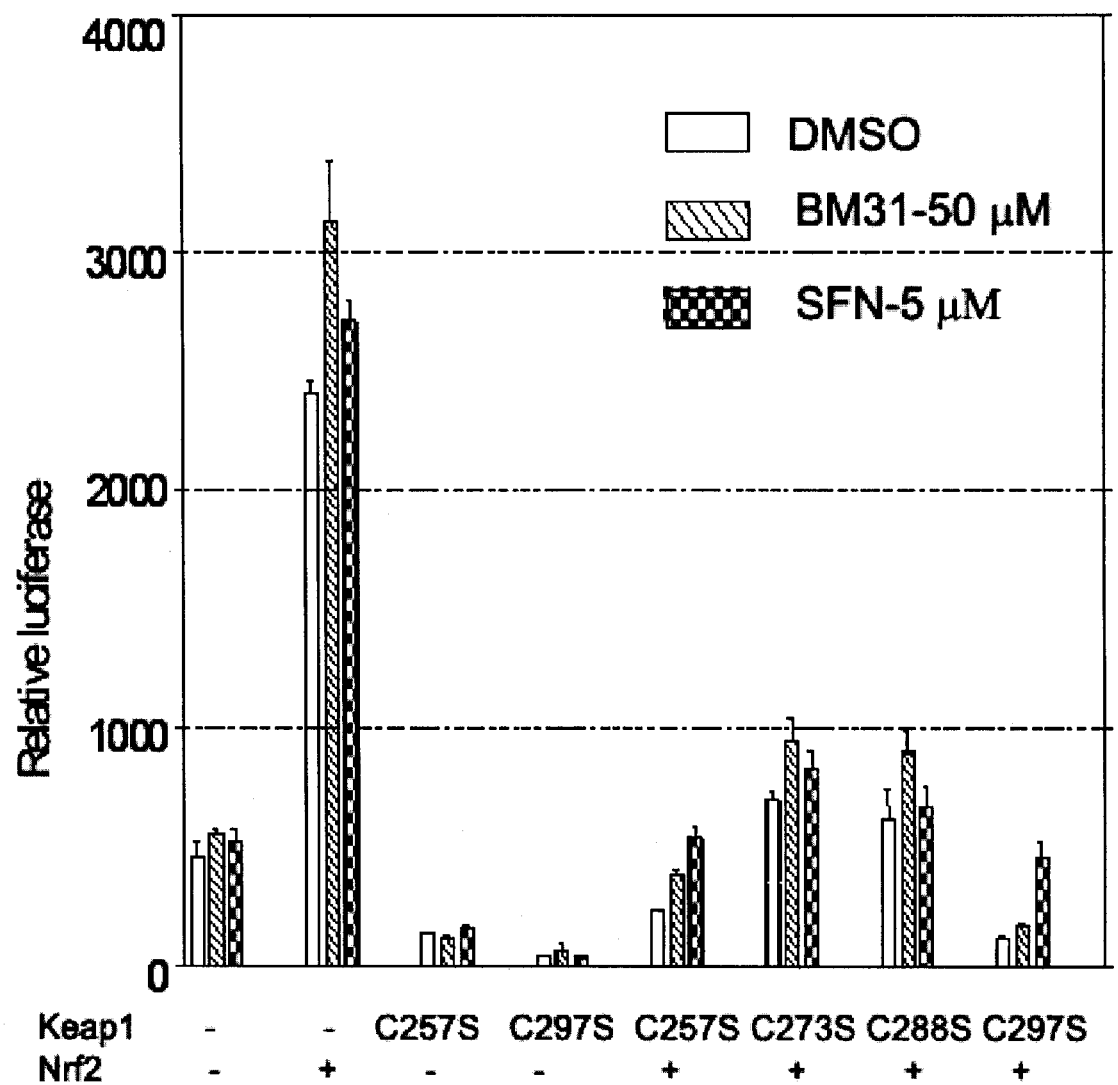
FIG. 4 illustrates the ARE-driven luciferase assays in 293T cells, demonstrating that Keap1 C297S mutant did not affect the potency of SFN, but abolished the Nrf2 induction activity of BM31.

Keap1 is a multi-domain protein, in which the IVR domain contains 4 cysteine residues, C257, C273, C288 and C297. The known Nrf2 inducers may interact with these cysteine residues in the IVR domain, resulting in conformational change of Keap1 and ultimately activating Nrf2. To investigate the role of these active cysteine residues in the Nrf2-inducing activity of BM31, 4 Keap1 mutants (C257S, C273S, C288S and C297S) are tested. BM31 is selected for this and further investigation because the dose-response is consistent for its capability in inducing Nrf2 nuclear translocation and induction of enzyme GCS (FIG. 3). Co-transfection experiments to investigate the effects of Keap1 IVR cysteine mutants on ARE-driven luciferase activities are performed. Specifically, 293T cells are co-transfected with ARE-driven pGL3 luciferase report vector, Keap1 vector with and without the Nrf2 expression vector (FIG. 4). After transfection, the cells are exposed to BM31 at 50 µM for 16 h before harvest. The cell lysates are used for measurement of ARE-driven luciferase activities. The data demonstrate that the compound BM31 potently induces the ARE-driven luciferase activities when cells are co-transfected with ARE-pGL3, Nrf2 and the C257S, C273S or C288S mutant Keap1 vectors. The results further demonstrate that the C273S and C288S Keap1 mutations led to the partial loss of basal level inhibition on Nrf2 by Keap1 and could constitutively activate the ARE-driven luciferase activities (FIG. 4), consistent with previous findings. However, it is found that the C273S and C288S mutations do not completely abolish the activity of BM31 or SFN in activating the ARE-driven luciferase activities (FIG. 4). In particular, our data demonstrated that Keap1 C297S mutant limits the potency of BM31 but not SFN in activating the ARE-driven luciferase activities (FIG. 4). Our conclusion is that BM31 targets the binding site around C297 in the IVR domain of Keap1, and mutation of residue C297 partially abolishes the Nrf2-inducing effect of BM31.

BM31 and SFP Enhance the Keap1-Nrf2 Association

Figure 5:
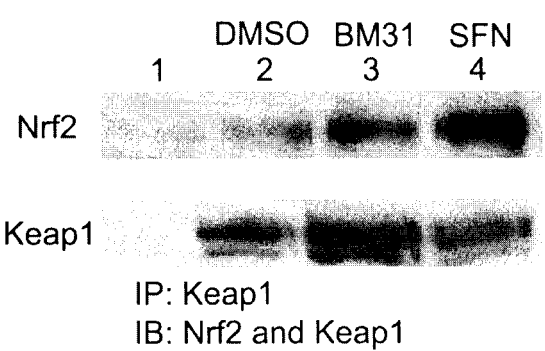
FIG. 5 illustrates 293T cell lysates immunoprecipitated with Keap1 antibody and the eluted proteins were immunoblotted with Nrf2 antibody. Lane 1: Nrf2 transfection; Lanes 2, 3, 4: Nrf2 and Keap1 co-transfection. Lanes 2, 3, 4: treated with DMSO, BM31 (50 µM) and SFN (5 µM), respectively.

To study the effect of BM31 on the interaction of Keap1 and Nrf2, Co-IP experiments are performed. 293T cells are successfully transfected and achieved high Nrf2 expression in this cell line. In the co-IP experiments, 293T cells are co-transfected with Nrf2 and Keap1 expression vectors. After transfection, the cells are treated with SFN and BM31 for 24 h before harvesting. The cell lysates are used for IP with Keap1 antibody. The eluted proteins are immunoblotted with Nrf2 antibody. The results reveal that treatment with BM31 or SFN increases the Nrf2/Keap1 complex (FIG. 5), indicating that BM31 may be inducing Nrf2 by modulating interaction between Keap1 and another protein partner in Keap1-Nrf2 pathway. For example, arsenic induces the Nrf2-dependent response through markedly enhancing the interaction between Keap1 and Cul3, subunits of the E3 ubiquitin ligase for Nrf2, which leads to impaired dynamic assembly/disassembly of the E3 ubiquitin ligase and thus decreases its ligase activity, resulting in inhibition of Nrf2 ubiquitination and degradation. Our further work will determine whether BM31 induces Nrf2 via a mechanism similar to that of arsenic.

BM31 Protects MCF-7 Cells from the Cytotoxic Damage of the Carcinogen B[a]P

Figure 6:
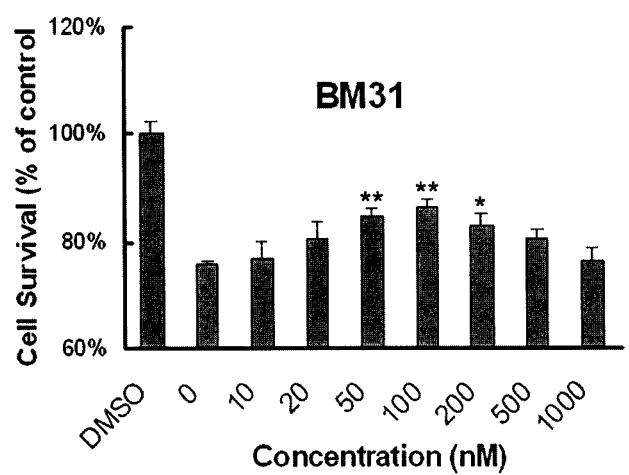
FIG. 6 illustrates the protective effect of BM31 for MCF-7 cells against the cytotoxic effect of 160 nM B[a]P. DMSO without B[a]P is included as a control. *$P<0.05$, **$P<0.006$ when compared with control 0 (DMSO with B[a]P). Experiments were performed in triplicate.
Figure 9:
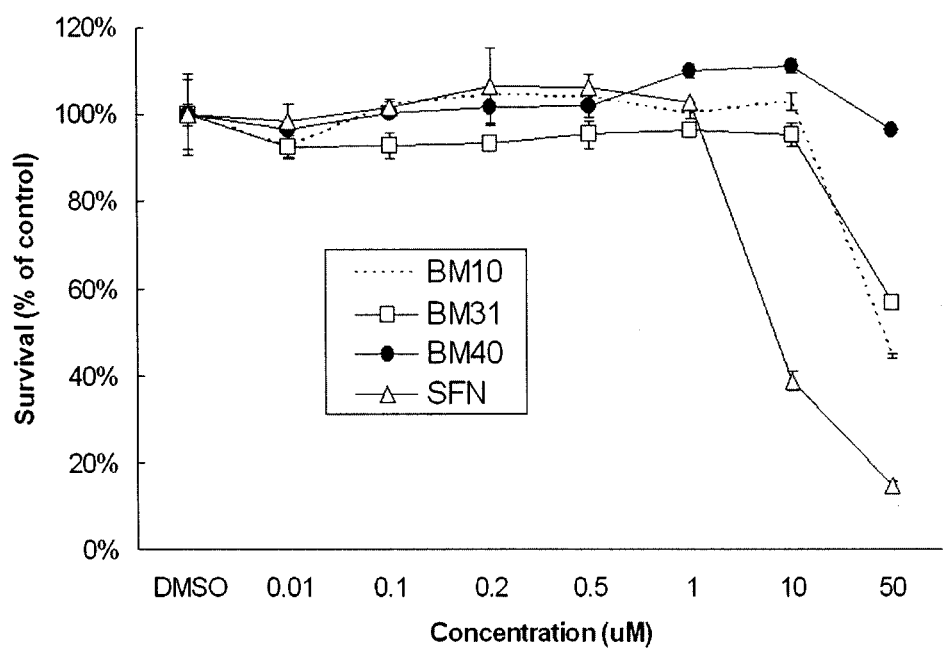
FIG. 9 illustrates MCF-7 cell survival curves for BM10, BM31, BM40 and SFN. MCF-7 cells were treated with test compounds at designated concentrations for 72 hours. Viable cells were evaluated by MTT assays. Experiments were performed in triplicate and repeated twice.

To test the capability of BM compounds in protecting against the cytotoxic effect of B[a]P, cellular assays using MCF-7 cells are performed. Incubation of MCF-7 cells with various concentrations of BM31 for 48 hours is followed by incubation with 160 nM B[a]P+the BM31 for 72 hours. MTT assays are performed to evaluate the protection effect of the BM31. DMSO without B[a]P was used as a control. As shown in FIG. 6, in the low dose range (from 50 nM to 200 nM), BM31 provides significant protection for the MCF-7 cells from the cytotoxic damage of the carcinogen B[a]P (FIG. 6). In addition, it is found that BM10, BM31 and BM40 do not have cytotoxic effects on the proliferation of MCF-7 cells in a broad dose range (10 nM to 10 µM), which distinguishes them from SFN (FIG. 9).

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed and claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

The invention claimed is:

1. A pharmaceutical composition comprising the compound of the formula:

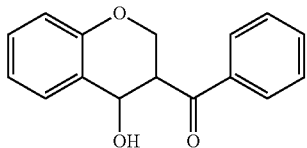

or a pharmaceutically acceptable salt thereof.

* * * * *